US011017902B2

(12) United States Patent
Sherkat et al.

(10) Patent No.: US 11,017,902 B2
(45) Date of Patent: May 25, 2021

(54) SYSTEM AND METHOD FOR PROCESSING HUMAN RELATED DATA INCLUDING PHYSIOLOGICAL SIGNALS TO MAKE CONTEXT AWARE DECISIONS WITH DISTRIBUTED MACHINE LEARNING AT EDGE AND CLOUD

(71) Applicant: Wise IOT Solutions, San Diego, CA (US)

(72) Inventors: Ebrahim Sherkat, San Diego, CA (US); Alex Wickstrom, San Diego, CA (US)

(73) Assignee: WISE IOT SOLUTIONS, San Diego, CA (US)

( * ) Notice: Subject to any disclaimer, the term of this patent is extended or adjusted under 35 U.S.C. 154(b) by 0 days.

(21) Appl. No.: 17/078,003

(22) Filed: Oct. 22, 2020

(65) Prior Publication Data
US 2021/0125722 A1 Apr. 29, 2021

Related U.S. Application Data

(60) Provisional application No. 62/926,335, filed on Oct. 25, 2019.

(51) Int. Cl.
G01N 33/48 (2006.01)
G01N 33/50 (2006.01)
(Continued)

(52) U.S. Cl.
CPC ......... G16H 50/20 (2018.01); G06K 9/00523 (2013.01); G06K 9/00557 (2013.01);
(Continued)

(58) Field of Classification Search
CPC .......... G16H 50/20; G16H 10/60; G06N 3/08; G06N 20/00; G06N 3/0454; G06N 5/04;
(Continued)

(56) References Cited

U.S. PATENT DOCUMENTS 10,084,868 B2 9/2018 Chandra et al.
10,599,666 B2 3/2020 Voigt et al.
(Continued)

FOREIGN PATENT DOCUMENTS

EP 3 637 730 A1 4/2020
WO WO 2017/042831 A2 3/2017
(Continued)

OTHER PUBLICATIONS

Lipton et al., Learning to Diagnose With LSTM Recurrent Neural Networks, ICLR 2016, arXiv:1511.03677v7 [cs.LG] Mar. 21, 2017, pp. 1-18.*

(Continued)

Primary Examiner — Guillermo M Rivera-Martinez
(74) Attorney, Agent, or Firm — Knobbe, Martens, Olson and Bear, LLP

(57) ABSTRACT

A system and method for processing human related data to make personalized and context aware decisions with distributed machine learning at an edge and a cloud is disclosed. A nearest edge computing device receives first, second and third sensed signals from first, second and third sensory devices, determines when the first, second and third sensed signals exceed corresponding thresholds, correlates pairs of the sensed signals to generate multiple correlation patterns, determines a lag time between the first sensed signal exceeding the first threshold and the second sensed signal exceeding the second threshold, provides each of the multiple correlation patterns and the lag time as inputs to multiple long short term memory (LSTM) neural networks, controls the multiple LSTM neural networks to provide outputs, and maps the patient to a stage of a medical condition based at least in part on the multiple correlation patterns and the lag time.

30 Claims, 25 Drawing Sheets

(51) Int. Cl.
  *G16H 50/20* (2018.01)
  *G16H 50/30* (2018.01)
  *G06K 9/00* (2006.01)
  *G06N 3/08* (2006.01)
  *G06N 3/04* (2006.01)

(52) U.S. Cl.
  CPC ............... *G06N 3/04* (2013.01); *G06N 3/08* (2013.01); *G16H 50/30* (2018.01)

(58) Field of Classification Search
  CPC ........ G06N 20/10; G06N 3/02; G06N 3/0481; G06K 2209/05; G06T 2207/20081; G06T 2207/20084
  See application file for complete search history.

(56) References Cited

U.S. PATENT DOCUMENTS

| | | | |
|---|---|---|---|
| 10,616,249 B2 | 4/2020 | C et al. | |
| 10,637,783 B2 | 4/2020 | Krishna Singuru | |
| 10,642,656 B2 | 5/2020 | Krishna Rao et al. | |
| 2008/0167538 A1* | 7/2008 | Teller | A61B 5/1118 600/301 |
| 2008/0242951 A1* | 10/2008 | Jung | A61B 5/411 600/300 |
| 2011/0224565 A1* | 9/2011 | Ong | G16H 50/20 600/509 |
| 2014/0235955 A1* | 8/2014 | Rao | A61B 5/0022 600/300 |
| 2016/0034809 A1* | 2/2016 | Trenholm | G06F 8/35 706/20 |
| 2018/0069933 A1* | 3/2018 | Chandra | H04L 67/18 |
| 2018/0103889 A1 | 4/2018 | Tzvieli et al. | |
| 2018/0182475 A1* | 6/2018 | Cossler | G16H 50/50 |
| 2018/0277246 A1* | 9/2018 | Zhong | G16H 10/60 |
| 2019/0369984 A1 | 12/2019 | Malladi et al. | |
| 2019/0370965 A1 | 12/2019 | Lay et al. | |
| 2020/0027210 A1 | 1/2020 | Haemei et al. | |
| 2020/0085312 A1* | 3/2020 | Tzvieli | A61B 5/7282 |
| 2020/0098464 A1* | 3/2020 | Velado | A61B 5/4839 |
| 2020/0113503 A1* | 4/2020 | Kim | A61B 5/14551 |
| 2020/0118458 A1* | 4/2020 | Shriberg | G16H 40/67 |
| 2020/0135334 A1* | 4/2020 | Rajasekhar | G10L 15/26 |
| 2020/0233403 A1 | 7/2020 | Gelbke et al. | |
| 2020/0302825 A1* | 9/2020 | Sachs | G09B 19/00 |
| 2020/0337648 A1* | 10/2020 | Saripalli | G06N 20/20 |
| 2020/0397383 A1* | 12/2020 | Genov | A61B 5/0476 |

FOREIGN PATENT DOCUMENTS

| | | |
|---|---|---|
| WO | WO 2018/020275 A1 | 2/2018 |
| WO | WO 2020/164879 A1 | 8/2020 |

OTHER PUBLICATIONS

Barik et al., "FogLearn: Leveraging Fog-Based Machine Learning for Smart System Big Data Analytics", *International Journal of Fog Computing*, vol. 1, issue 1, Jan.-Jun. 2018, in 21 pages.

Kraemer et al., "Fog Computing in Healthcare—A Review and Discussion", *IEEE Access*, vol. 5, 2017, pp. 9206-9222.

Oueida et al., "An Edge Computing Based Smart Healthcare Framework for Resource Management", *Sensors*, vol. 18, No. 4307, 2018, in 22 pages.

Notification of Transmittal of the International Search Report and the Written Opinion of the International Searching Authority, or the Declaration and International Search Report for the International Application No. PCT/US2020/057127 dated Mar. 15, 2021.

* cited by examiner

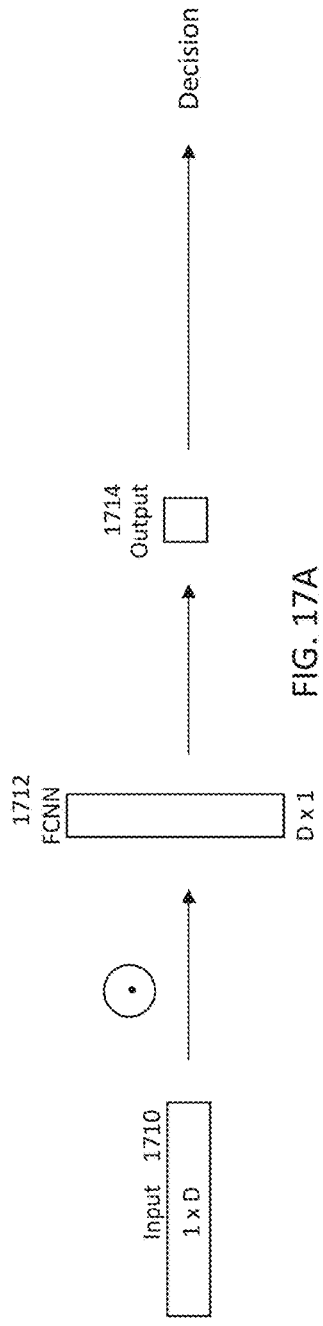
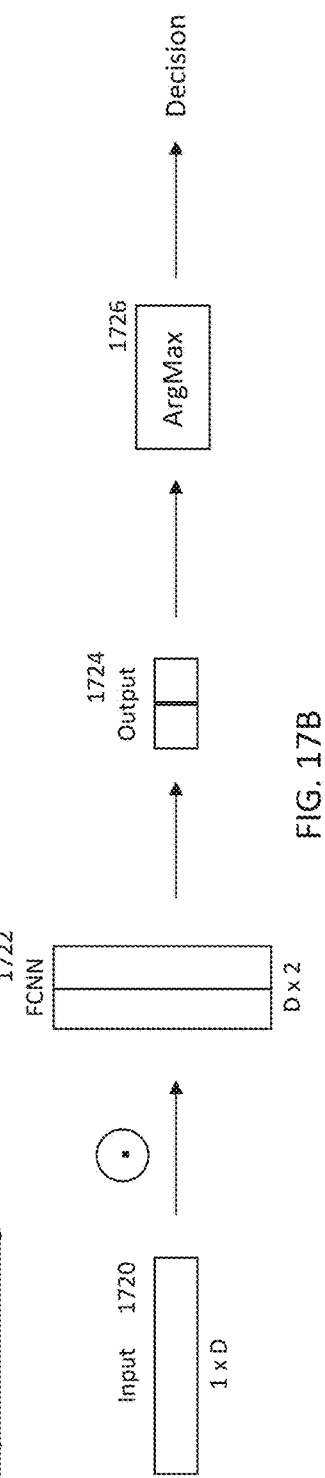
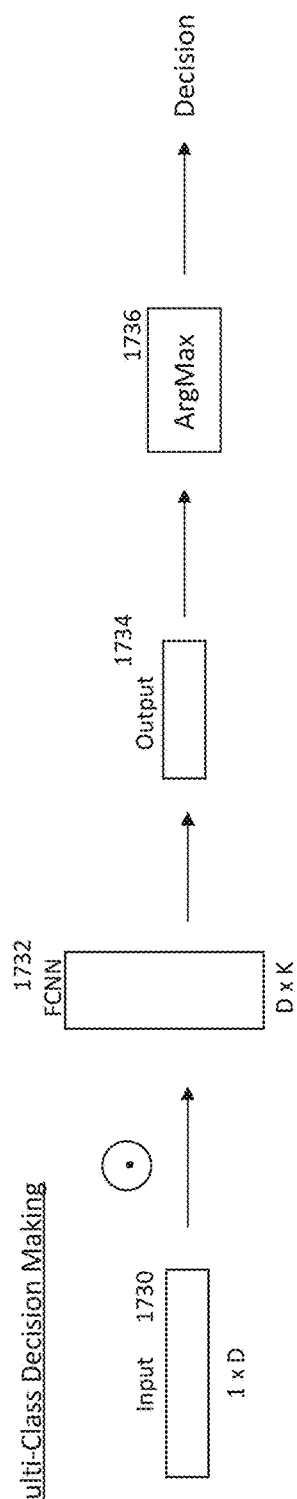
FIG. 17A
FIG. 17B
FIG. 17C

SYSTEM AND METHOD FOR PROCESSING HUMAN RELATED DATA INCLUDING PHYSIOLOGICAL SIGNALS TO MAKE CONTEXT AWARE DECISIONS WITH DISTRIBUTED MACHINE LEARNING AT EDGE AND CLOUD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims benefit of U.S. Provisional Application No. 62/926,335, filed on Oct. 25, 2019, entitled System and Method for Processing Human Related Data Including Physiological Signals to Make Context Aware Decisions with Distributed Machine Learning at Edge and Cloud.

BACKGROUND

Field

The described technology generally relates to artificial intelligence in medical decision making, and in particular processing human physiological signals over varying periods of time to make a medical decision.

Description of the Related Technology

The use of computerized medical decision support in a hospital or clinical setting is known.

SUMMARY

One inventive aspect provides prediction of acute heart failure or prediction of other adverse events in heart diseases (e.g., orthostatic hypertension, myocardial infarction).

Another aspect is automated diagnosis of four different classes of heart failure and classification of all heart failure patients into these four classes based on guidelines of heart health related organizations such as the New York Heart Association or the American College of Cardiology.

Another aspect is to classify all heart failure patients into a particular subtype, such as reduced ejection fraction (EF) or preserved EF; systolic vs. diastolic heart failure; right ventricular vs. left ventricular heart failure (such as using a semi-supervised or scattering embodiment).

Another aspect is to provide edge technology for advanced telemedicine for a cardiologist and internal medicine (primary care). This technology enables healthcare professionals to see all physiological signals in a history between visits, to store notes and data from each physical examination, and aggregate all the information in the edge for anomaly detection of blood pressure (BP), heart rate (HR), heart rate variability (HRV). This can be used for prevention as well as for diagnosis or prediction of adverse events.

Physiological signal changes may happen over an extended period of time (an hour or more) at least a few hours prior to an acute heart failure. The described technology can detect the changes in real time and let the doctor intervene in a timely manner to avoid adverse events such as acute heart failure.

In some embodiments, the described technology's correlation, multi-level recurrent neural network (RNN) and long short-term memory (LSTM) with an attention network and a memory aggregator can learn and detect a long temporal history of physiological signal changes in a novel way and therefore identify the patient's risk.

For example, correlation of signals and multi-level LSTM can learn longer term temporal history than any other method by utilizing the attention network and the memory aggregator. A two dimensional (2-D) attention heat map learned over multiple signals and multiple states can provide an interpretable artificial intelligence (AI) result that can explain which portion of input signals or features result in the decision that the AI system makes. The interpretable AI can readily be explained to a doctor and builds their trust for adoption better than any other black box AI. Due to the method using correlation between signals and the interpretable attention heat map, the system needs much less data to train the network. A group of cardiologists can help to label recorded data and suggest new intermediate nodes to the machine learning (ML) method to help explain decision making of the ML(AI) models. The system can include multiple processes for decision making.

Another aspect relates to a system for processing human related data to make personalized and context aware decisions with distributed machine learning at an edge and a cloud, the system comprising a plurality of edge computing devices configured to communicate data with each other, the plurality of edge computing devices physically spaced apart from each other; at least three sensory devices comprising first, second and third sensory devices configured to sense a patient's physiological signal in real time to generate a first sensed signal, a second sensed signal and a third sensed signal and communicate the first, second and third sensed signals to an edge computing device nearest available to the first, second and third sensory devices among the plurality of edge computing devices; and a core cloud network configured to communicate with the edge computing devices or the at least three sensory devices, the nearest available edge computing device being in data communication with the core cloud network and configured to receive the first, second and third sensed signals from the first, second and third sensory devices; determine when the first sensed signal exceeds a first threshold for a first predetermined time; determine when the second sensed signal exceeds a second threshold for a second predetermined time; determine when the third sensed signal exceeds a third threshold for a third predetermined time; correlate the first sensed signal and the second sensed signal to generate a first correlation pattern; determine a lag time between the first sensed signal exceeding the first threshold and the second sensed signal exceeding the second threshold; provide the first correlation pattern and the lag time as inputs to a first long short term memory (LSTM) neural network; correlate the second sensed signal and the third sensed signal to generate a second correlation pattern; provide the second correlation pattern to a second LSTM neural network as an input; control the first LSTM neural network and the second LSTM neural network to provide outputs; and map the patient to a stage of a medical condition based at least in part on the first correlation pattern, the lag time and the second correlation pattern.

The nearest available edge computing device may be further configured to correlate the first sensed signal and the third sensed signal to generate a third correlation pattern; provide the third correlation pattern to a third LSTM neural network as an input; collect a history of states from each of the first, second and third LSTM neural networks; analyze the history of the states using an attention network such that an output of the attention network learns interactions across time and across signals; and summarize a history of the interactions using a multi-signal memory aggregator such that an output of the multi-signal memory aggregator is fed into a decision making module to map the patient to the stage of the medical condition based on the summarized history of the interactions.

The nearest available edge computing device nay comprise a first feature extractor configured to determine when the first sensed signal exceeds the first threshold for the first predetermined time; a second feature extractor configured to determine when the second sensed signal exceeds the second threshold for the second predetermined time; a third feature extractor configured to determine when the third sensed signal exceeds the third threshold for the third predetermined time; and a first correlator configured to correlate the first sensed signal and the second sensed signal to generate the first correlation pattern and determine the lag time between the first sensed signal exceeding the first threshold and the second sensed signal exceeding the second threshold as inputs to a first cell in the first LSTM neural network in an LSTM bank, wherein the third feature extractor is configured to directly feed the third sensed signal to a first cell in the second LSTM neural network in the LSTM bank, wherein the first correlator is further configured to generate additional first correlation patterns over time into additional different cells of the first LSTM neural network, wherein the third feature extractor is further configured to provide additional instances over time when the third sensed signal exceeds the third threshold as input signals into additional different cells of the second LSTM neural network, wherein the cells of each of the first LSTM neural network and the cells of the second LSTM neural network in the LSTM bank are configured to be fed into a fully connected neural network to generate attention map coefficients that are component-wise multiplied with the cells of the first LSTM neural network and the cells of the second LSTM neural network to generate an attention map, wherein the attention map is configured to be fed into the multi-signal memory aggregator to aggregate multiple signal memories over time to prepare an optimal input into the decision making module, and wherein the decision making module is configured to make a decision to map the patient to the stage of the medical condition based on the optimal input received from the multi-signal memory aggregator.

The first sensed signal, the second sensed signal and the third sensed signal may be of different modalities, wherein the first correlation pattern, the second correlation pattern, a state of the first LSTM neural network and a state of the second LSTM neural network may be configured to be fed into a first multi-modal LSTM neural network, wherein the second correlation pattern, the third correlation pattern, the state of the second LSTM neural network and a state of the third LSTM neural network may be configured to be fed into a second multi-modal LSTM neural network, and wherein the states of the first, second and third LSTM neural networks, and outputs of the first multi-modal LSTM neural network and the second multi-modal LSTM neural network may be configured to be fed into a multi-signal memory aggregator.

The system may further comprise an attention function processor configured to receive one of the first, second and third sensed signals as an input signal; find one or more certain patterns of the input signal; and categorize the input signal and generate the attention map corresponding to the certain patterns before being correlated.

The system may further comprise an attention function processor configured to receive one of the first, second and third sensed signals as an input signal; find one or more certain patterns of the input signal; and categorize the input signal and generate the attention map corresponding to the certain patterns before being an input of one of the first or second multi-modal LSTM neural networks.

The nearest available edge computing device may be configured to present the attention map to a healthcare professional as documentation to support the determination of the stage of the patient's medical condition.

The decision making module may comprise at least one fully connected neural network. The decision making module may be configured to generate a scalar quantified risk score. The fully connected neural network may comprise a scaled sigmoid activation function. The decision making module may comprise an argmax function configured to operate on an output of the fully connected neural network. The decision making module may be configured to generate a binary format prediction. The fully connected neural network may comprise a unit for each class of a multiple-class classification and wherein the output of the argmax function is a probability of the input data belonging to each class of the multiple-class classification.

The nearest available edge computing device may comprise at least one of the first to third LSTM neural networks and the decision making module. The nearest available edge computing device may be configured to buffer and align at least one of the first, second and third sensed signals before being correlated.

In another aspect there is an edge computing device for processing human related data to make personalized and context aware decisions with distributed machine learning at an edge and a cloud, the edge computing device comprising a memory storing computer executable instructions; and a processor in data communication with the memory and, when executed by the executable instructions, configured to receive a first sensed signal, a second sensed signal and a third sensed signal obtained in real time from sensing a patient's physiological signal from first, second and third sensory devices, determine when the first sensed signal exceeds a first threshold for a first predetermined time, determine when the second sensed signal exceeds a second threshold for a second predetermined time, determine when the third sensed signal exceeds a third threshold for a third predetermined time, correlate the first sensed signal and the second sensed signal to generate a first correlation pattern, determine a lag time between the first sensed signal exceeding the first threshold and the second sensed signal exceeding the second threshold, and correlate the second sensed signal and the third sensed signal to generate a second correlation pattern; a first long short term memory (LSTM) neural network configured to receive the first correlation pattern and the lag time from the processor; and a second long short term memory (LSTM) neural network configured to receive the second correlation pattern from the processor, wherein the processor is further configured to control the first LSTM neural network and the second LSTM neural network to provide outputs; and map the patient to a stage of a medical condition based at least on the first correlation pattern, the lag time and the second correlation pattern.

The processor may be further configured to correlate the first sensed signal and the third sensed signal to generate a third correlation pattern; and provide the third correlation pattern to a third LSTM neural network as an input, wherein the processor may be configured to make a decision on outputs of the first, second and third LSTM neural networks.

The processor may be further configured to make the decision by performing a scattering function on the outputs of the first, second and third LSTM neural networks.

The processor may be further configured to correlate the first sensed signal and the third sensed signal to generate a third correlation pattern; provide the third correlation pattern to a third LSTM neural network as an input; collect a history of states from each of the first, second and third LSTM neural networks; analyze the history of the states using an attention network such that an output of the attention network learns interactions across time and across signals; summarize a history of the interactions using a multi-signal memory aggregator; and feed an output of the multi-signal memory aggregator into a decision making module to map the patient to the stage of the medical condition based on the summarized history of the interactions.

The processor may comprise a first feature extractor configured to determine when the first sensed signal exceeds the first threshold for the first predetermined time; a second feature extractor configured to determine when the second sensed signal exceeds the second threshold for the second predetermined time; a third feature extractor configured to determine when the third sensed signal exceeds a third threshold for a third predetermined time; and a first correlator configured to correlate the first sensed signal and the second sensed signal to generate the first correlation pattern and determine the lag time between the first sensed signal exceeding the first threshold and the second sensed signal exceeding the second threshold as inputs to a first cell in the first LSTM neural network in an LSTM bank, wherein the third feature extractor is configured to directly feed the third sensed signal to a first cell in the second LSTM neural network in the LSTM bank, wherein the first correlator is further configured to generate additional first correlation patterns over time into additional different cells of the first LSTM neural network, wherein the third feature extractor is further configured to provide additional instances over time when the third sensed signal exceeds the third threshold as input signals into additional different cells of the second LSTM neural network, wherein the cells of each of the first LSTM neural network and the cells of the second LSTM neural network in the LSTM bank are configured to be fed into a fully connected neural network to generate attention map coefficients that are component-wise multiplied with the cells of the first LSTM neural network and the cells of the second LSTM neural network to generate an attention map, wherein the attention map is configured to be fed into a multi-signal memory aggregator to aggregate multiple signal memories over time to prepare an optimal input into a decision making module, and wherein the decision making module is configured to make a decision to map the patient to the stage of the medical condition based on the optimal input received from the multi-signal memory aggregator.

In yet another aspect, there is a method of processing human related data to make personalized and context aware decisions with distributed machine learning at an edge computing device in communication with a cloud, the method comprising receiving, at a processor of the edge computing device, a first sensed signal, a second sensed signal and a third sensed signal obtained from sensing a patient's physiological signal from first, second and third sensory devices; determining, at the processor, when the first sensed signal exceeds a first threshold for a first predetermined time, determining, at the processor, when the second sensed signal exceeds a second threshold for a second predetermined time, determining, at the processor, when the third sensed signal exceeds a third threshold for a third predetermined time; correlating, at the processor, the first sensed signal and the second sensed signal to generate a first correlation pattern, determining, at the processor, a lag time between the first sensed signal exceeding the first threshold and the second sensed signal exceeding the second threshold; correlating, at the processor, the second sensed signal and the third sensed signal to generate a second correlation pattern; receiving, at a first long short term memory (LSTM) neural network of the edge computing device, the first correlation pattern and the lag time; receiving, at a second LSTM neural network of the edge computing device, the second correlation pattern; controlling, at the processor, the first LSTM neural network and the second LSTM neural network to provide outputs; and mapping, at the processor, the patient to a stage of a medical condition based at least on the first correlation pattern, the lag time and the second correlation pattern.

The method may further comprise correlating, at the processor, the first sensed signal and the third sensed signal to generate a third correlation pattern; receiving, at a third LSTM neural network of the edge computing device, the third correlation pattern; collecting, by the processor, a history of states from each of the first, second and third LSTM neural networks; analyzing, at an attention network of the edge computing device, the history of the states to learn interactions across time and across signals; summarizing, at a multi-signal memory aggregator of the edge computing device, a history of the interactions; feeding, by the processor, an output of the multi-signal memory aggregator into a decision making module of the edge computing device; and mapping, at the decision making module, the patient to the stage of the medical condition based on the summarized history of the interactions.

The method may further comprise receiving first correlation pattern inputs at a first cell of the first LSTM neural network in an LSTM bank; directly receiving the third sensed signal when the third sensed signal exceeds the third threshold at a first cell in the second LSTM neural network in the LSTM bank; receiving additional first correlation patterns over time into additional different cells of the first LSTM neural network; receiving, by the processor, additional instances over time when the third sensed signal exceeds the third threshold as input signals into additional different cells of the second LSTM neural network; generating, by an attention network of the edge computing device, attention map coefficients based on the cells of each of the first LSTM neural network and the cells of the second LSTM neural network in the LSTM bank to be fed into a fully connected neural network; generating, by the attention network, an attention map based on the attention map coefficients that are component-wise multiplied with the cells of the first LSTM neural network and the cells of the second LSTM neural network; feeding, by the processor, the attention map into a multi-signal memory aggregator that is configured to aggregate multiple signal memories over time; and mapping, at a decision making module, the patient to the stage of the medical condition based on the aggregated multiple signal memories received from the multi-signal memory aggregator.

The edge computing device may be a nearest available edge computing device to the patient among a plurality of edge computing devices comprising the first to third edge computing devices being in data communication with the cloud.

The method may further comprise receiving a request for service from a sensory device of the patient; locating the patient's sensory device; determining that the edge computing device is a nearest available edge computing device to the patient sensory device of a plurality of edge computing devices comprising the first to third edge computing devices being in communication with the cloud; and assigning a service slot to the patient's sensory device. Determining the nearest available edge computing device may comprise receiving, at the plurality of edge computing devices, a signal sent by the patient's sensory device; measuring strengths of the signal received by the plurality of edge computing devices; comparing the strengths of the received signal; and determining an edge computing device to have a strongest signal strength as the nearest available edge computing device.

The method may further comprise buffering and aligning one of the first sensed signal or the second sensed signal before the correlating. The method may further comprising finding one or more certain patterns of the first sensed signal or the second sensed signal; and generating an attention map corresponding to the certain patterns before the correlating. The method may further comprise presenting the attention map to a healthcare professional as documentation to support the determination of the stage of the patient's medical condition.

In another aspect, there is a system for processing human related data to make personalized and context aware decisions with distributed machine learning at an edge and a cloud, the system comprising a plurality of edge computing devices configured to communicate data with each other, the plurality of edge computing devices physically spaced apart from each other; at least two sensory devices comprising first and second sensory devices configured to sense a patient's physiological signal in real time to generate a first sensed signal and a second sensed signal and communicate the first and second sensed signals to a first edge computing device nearest available to the first and second sensory devices among the plurality of edge computing devices; and a core cloud network configured to communicate with the edge computing devices or the at least two sensory devices, the nearest edge computing device in data communication with the core cloud network and configured to receive the first and second sensed signals from the first and second sensory devices; determine when the first signal exceeds a first threshold for a first predetermined time and subsequently determine when the second signal exceeds a second threshold for a second predetermined time; correlate the first signal and the second signal to generate a first correlation pattern; determine a lag time between the first signal exceeding the first threshold and the second signal exceeding the second threshold; and provide the first correlation pattern and the lag time as inputs to at least two recurrent neural networks (RNNs) operatively connected to each other to provide an input to a decision making module to map the patient to a stage of a medical condition based at least on one or more of the first correlation patterns and the lag time.

BRIEF DESCRIPTION OF THE DRAWINGS

FIG. 17A is a block diagram of an embodiment of decision making that outputs a scalar.

FIG. 17B is a block diagram of an embodiment of decision making that outputs a binary decision.

FIG. 17C is a block diagram of an embodiment of decision making that outputs a multi-class decision.

DETAILED DESCRIPTION OF CERTAIN EMBODIMENTS

As described in various example embodiments, a system and method for processing human related data including physiological signals are disclosed to make context aware decisions with distributed machine learning at edge and cloud. Although the example embodiments are described with respect to a particular system for decision making using distributed cloud and edge computing and machine learning, the described technology is not limited to the disclosed embodiments.

Figure 1:
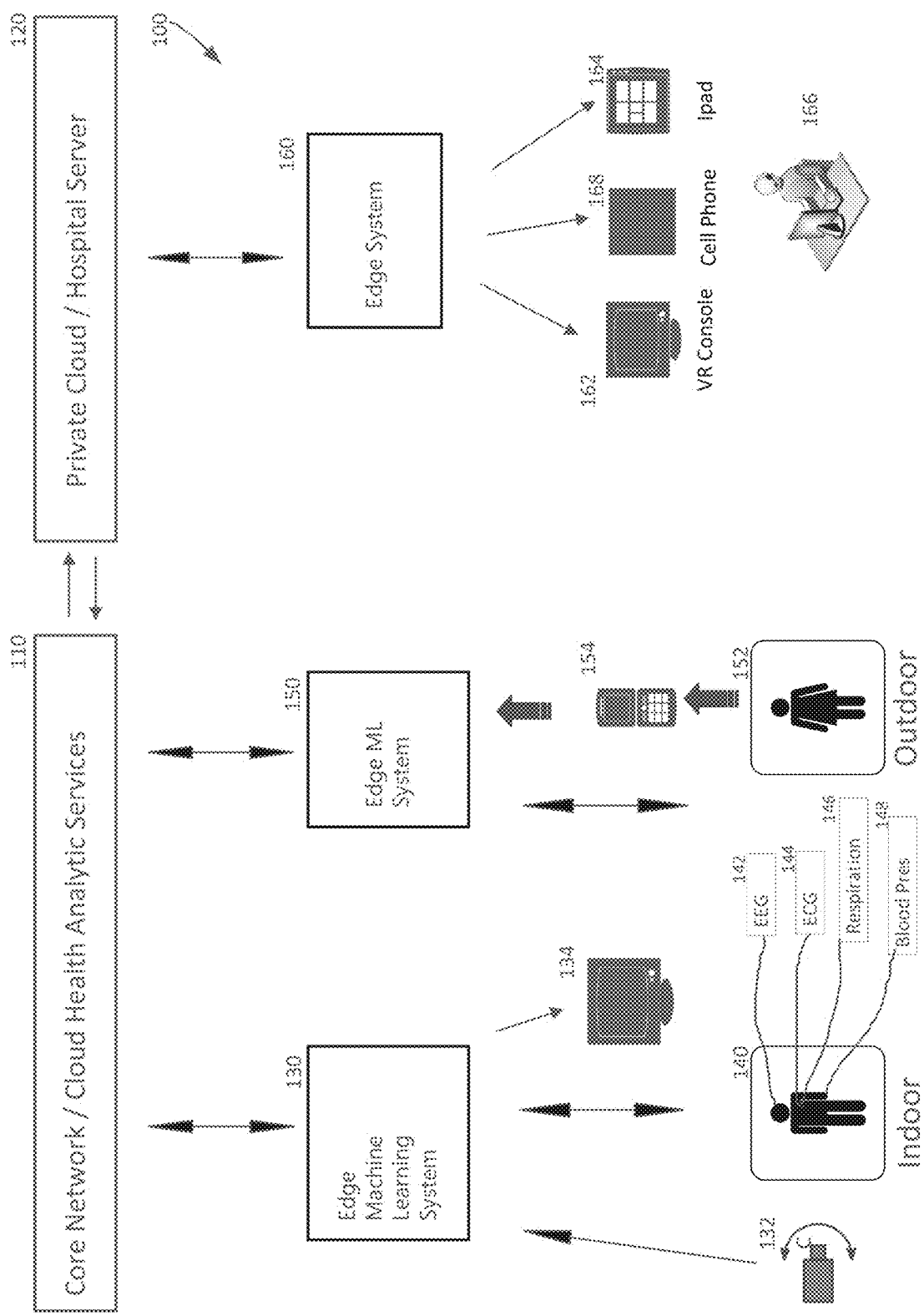
FIG. 1 is a high level block diagram of an embodiment of a system for decision making using distributed edge computing and machine learning.

FIG. 1 is a high level block diagram of an embodiment of a system 100 for decision making using distributed cloud and edge computing and machine learning. The decision making system 100 shown in FIG. 1 is merely an example, and can have different structures, shapes, and/or user interfaces. The components of the system 100 may be directly or indirectly connected to each other. The components of the system 100 may also be in wired or wireless connection with each other. Furthermore, certain components may be removed (e.g., optional) or others can be added to the decision making system 100, and this can be applied to the block diagrams of the other figures. The system 100 includes a core network/cloud health analytic services system 110, a private cloud/hospital server 120, an edge machine learning (ML) system 130 and one or more other edge ML systems 150, and an edge ML system 160.

In some embodiments, the edge ML system 130 and the one or more other edge ML systems 150 interconnect with the core network cloud health analytic services system 110 by wired or wireless connections. Wired connections may include use of a local area network, wide area network, the Internet and others, and may include use of the Ethernet or other standards. Wireless connectivity may include use of Wi-Fi or cellular connections using 4G, LTE, 5G or other standards.

The system 100 can also include one or more fixed or mobile devices, such as a camera or video camera 132, and devices to measure certain human physiological signals, including, but not limited to, an electroencephalogram (EEG) 142, an electrocardiogram (ECG) 144, respiration 146 and blood pressure 148 for an indoor patient 140 or an outdoor patient 152. In some embodiments, these devices 132 and 142-149 communicate data with one or more edge devices, such as 130 or 150, in its vicinity using, for example, wireless or wireline protocols.

The edge ML system 130 can be located in a patient's home. It can receive physiological signals captured by sensor devices such as wearables or patches located on a patient body or implants inside their body through one or more wireless protocols. These sensor devices can be initialized or configured by over the air software update.

The system 100 can also include a display 134 connected to the edge ML system 130 with wired, wireless or wireline protocols. Captured signals may include, but are not limited to, ECG, photoplethysmography (PPG), respiration, bio-impedance of a lung or other part of body (congestion), blood pressure (BP), pulse oximeter ($SPO_2$ blood oxygen level), electromyography (EMG), EEG, physical activity or accelerometer data, face expression, angle of arrival and or time of arrival to locate patient and/or depth information, heart beating, and voice or any audio signal from patient including background noise. The outdoor patient 152 wearables or patches may communicate with the edge ML system 150 or any nearer edge ML system directly or through a phone or watch.

The sensor device periodically sends a unique signal such as a beacon and all edge systems in a vicinity receive that signal and measure the signal strength of the received signal. The edge systems coordinate with each other the measured signal strengths and the edge system with a highest received signal strength designates a channel for that sensory device to start a link and communicate with the edge system.

The private cloud/hospital server 120 can be in wired or wireless communication with the edge system 160 that may include machine learning and augmented reality (AR)/virtual reality (VR). In institutions such as a hospital or outpatient clinics (doctor offices) one can use the edge system 160, for example, to have AR/VR capability for performing remote procedures with healthcare professionals including but not limited to doctors, physician assistants or nurses for advance telemedicine or colonoscopy or other services.

In some embodiments, as part of the core network/cloud health analytic services system 110 (hereinafter to be interchangeably used with the cloud), a cloud monitoring center providing health and analytics services receives all physiological data from a large number of edge devices located in patients' homes and stores data in its database (see FIG. 4B). The cloud 110 can be platform independent (using container, it can be run on Amazon AWS, Microsoft Azure, Google, or other providers) and through the core network it may connect to the private cloud/hospital servers 120 of other institutions including, but not limited to, health systems, hospitals, outpatient clinics, medical groups, transitional care, nursing homes, rehabilitation centers, and home health care agencies. The cloud monitoring center may integrate electronic medical records (EMR) of any institution such as health systems or hospitals through a flexible API (such as shown in FIG. 4B).

Each mobile device can go through a discovery mode when it is turned on or when it wakes up from sleep by sending a request for service. Edge devices, such as 130 and 150, may be in listening mode and after locating the new device, the closest edge may assign a service slot to the new device. Each edge device can be connected to a core network (cloud) 110 through a communication link. In addition, adjacent edge devices can communicate directly for lower latency applications when a mobile device needs to be handed off to the new edge device and it is traveling fast, for example. These fixed or mobile devices could be any device including, but not limited to, wearables (such as watches, garment, belts or other wearable devices), patches or sticks on the body, implants inside body, phone, video camera, sensors (temperature, air pressure, air quality), actuators, robots, tablet, laptop, TV, display, appliances, drones, cars, buses (and cameras on them), trains, bikes, scooters, and motor cycles.

The edge ML systems 130 and 150 can be a gateway or hub that has machine learning and decision-making capability and can provide different automated services. In one embodiment, referred to as health management, it can merge all data from cameras and other sensing devices such as voice and vital signs and perform semi-supervised learning algorithm to determine face expression, emotion, the health and safety of patient or suggest a right diet. In another embodiment, at least one of the edge ML systems 130 and 150 can make decisions with minimum latency for serious problems such as prediction of acute heart failure and provide insight with an interpretive report to the doctor to intervene and take corrective action. At least one of the edge ML systems 130 and 150 can incorporate any model and parameters from supervised learning of a bigger data set residing in the cloud 110. The edge gateway may be located inside home, at light pole in street, in the car or in the hospital and can be connected to the core network through wired or wireless communication and can be updated over the air. The latest model and parameters can be pushed to the edge ML systems 130 and 150 over the air that provides service such as feedforward decision making regarding the risk of acute heart failure (providing a risk score) or predicting acute heart failure. The latest AI or ML models and parameters can be pushed to the edge ML systems 130 and 150 that provide service remotely inside a patient's home or inside a business, office or factory, for example.

Figure 4A:
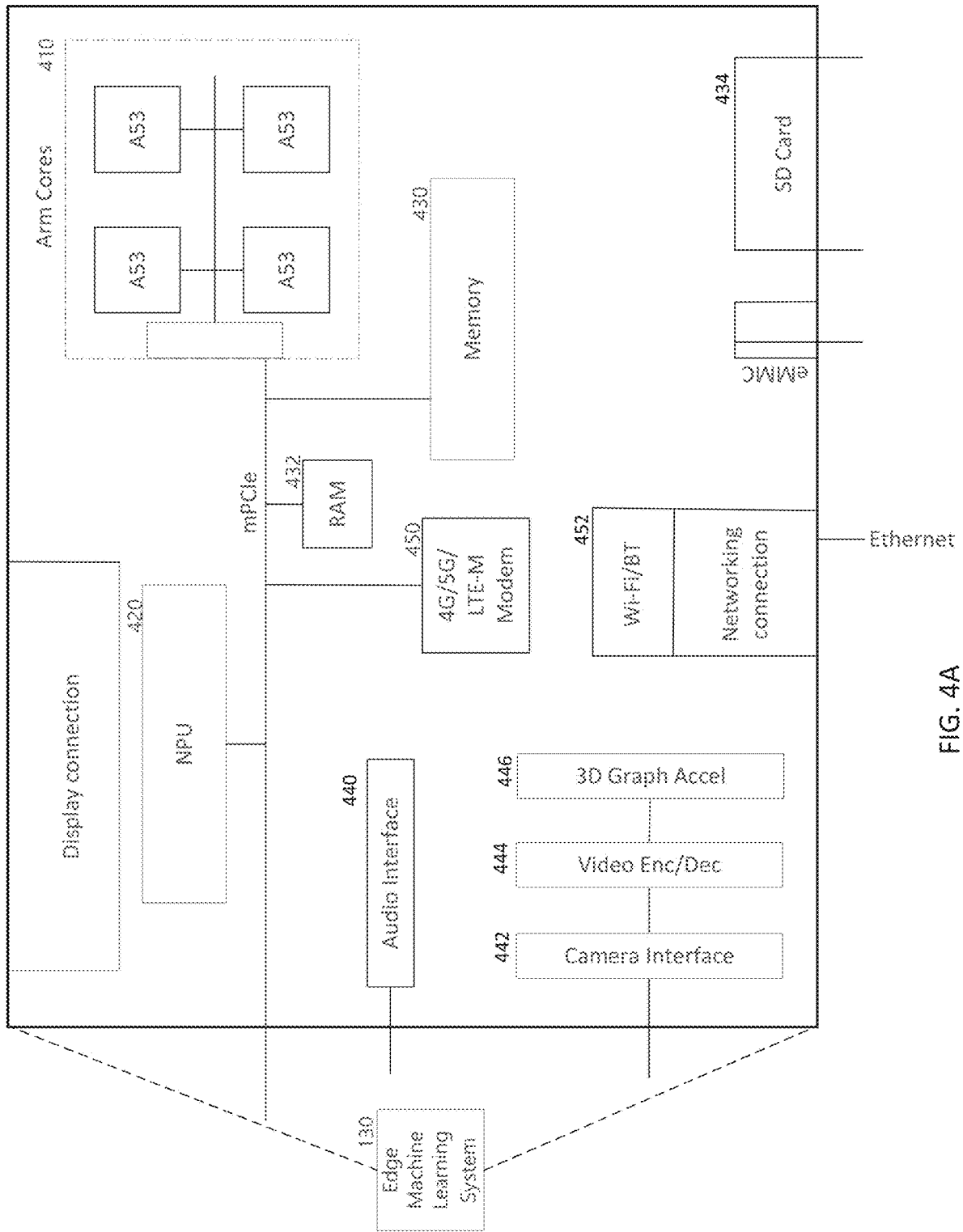
FIG. 4A is a block diagram of an embodiment of an edge machine learning system such as identified in FIG. 1.
Figure 4B:
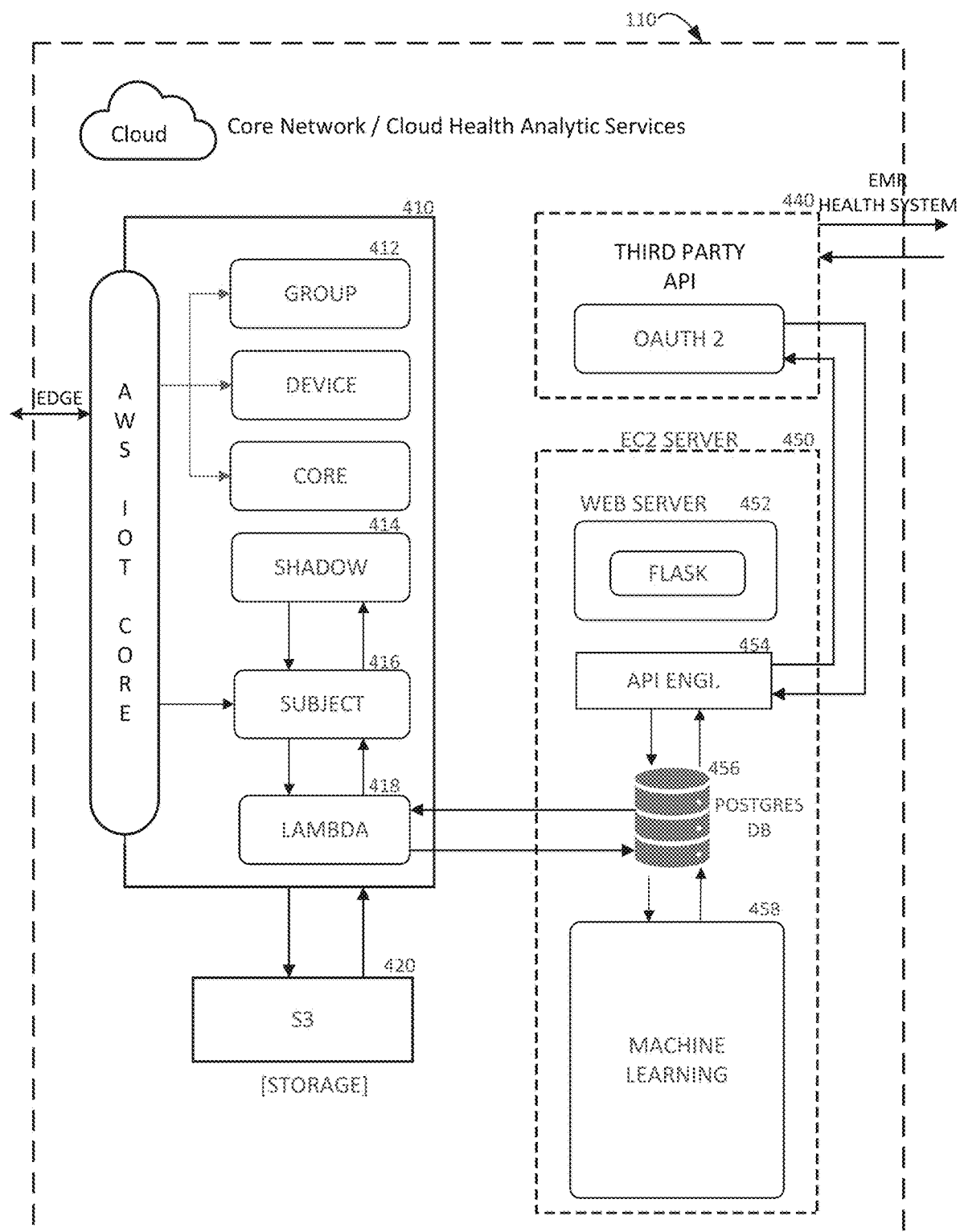
FIG. 4B is a block diagram of an embodiment of a core network/cloud health analytic services such as identified in FIG. 1.

FIG. 4A is a block diagram of an embodiment of an edge machine learning system such as identified in FIG. 1. Example internal blocks of the edge ML systems 130 and 150 are shown in FIG. 4A. A quad-core ARM processor 410 (four A53) is an example of a CPU inside the edge system 130, 150. A neural processing unit (NPU) 420 is a hardware accelerator to perform, for example, Tensor operations required for neural network models. The NPU 420 can be obtained from ARM or Samsung, for example. The NPU 420 can perform the forward path (inference) of neural network models on inputs from multiple sensors at a much higher speed and can achieve lower inference time compared to running on an ARM even with an existing software accelerator such as an ARM NN. Therefore, the novel machine learning algorithms described herein can operate on the edge in real time and achieve very low latency. The edge system 130, 150 includes a sufficient memory 430 to buffer sensory device inputs and enough RAM 432 to process them in real time with the NPU 420 and CPU 410. The edge system 130, 150 may have a built-in 4G/5G/LTE-M cellular modem 450 that can receive over-the-air updates of models and transmit over-the-air machine learning results. The edge system 130, 150 includes a built-in Wi-Fi and BLE modem 452 for wireless communication with cameras or with wearables, patches and implants that capture physiological signals.

The edge system 130, 150 may also include multimedia interfaces such as an audio interface 440, a camera interface 442, a video encoder and decoder 444, and a 3-D graphic accelerator 446. The edge system 130, 150 may further include an SD card interface 434 (for flash memory) that can be used to boot the edge, load applications or save data in case of network or Internet disconnection for later recovery.

State of the art machine learning models can be trained to run on the edge system 130, 150 for face expression, face recognition, image segmentation and processing to see inside a mouth or an ear of a patient for advanced telemedicine.

The edge gateway can provide different services and connect to different devices through different radio access protocols depending on data rate, required mobility and latency required for that service. The edge gateway can be used for all three type of use cases in 5G: high throughput use case, low latency use case, and large number of devices use case. Some applications or services may require a combination of two or three 5G capabilities or use cases such as traffic control, industrial Internet of Things (IOT), remote surgery, smart home and health management or smart city.

To help with capacity and latency, different devices may be assigned to different beams depending to their location, where the beam direction and beam width are adaptive and can depend on locations of mobile devices at a given time. On the edge system, a bigger antenna array may be used rather than on the mobile device.

FIG. 4B is a block diagram of an embodiment of a core network/cloud health analytic services such as identified in FIG. 1. An overview of a cloud architecture for the cloud 110 is illustrated in FIG. 4B. An AWS IoT Core 410 includes a group 412, a device, a core, a shadow 414, a subject 416 and a Lambda 418. Different edge devices can be assigned into different groups 412 based on their intended use (e.g., heart failure prediction). The shadow 414 of each edge device can be maintained in the cloud, which makes the state of the device available even if the device is disconnected from the AWS IoT Core 410. This allows the system to continue to collect and report data about device state if devices go offline. It also allows other AWS services to request changes to device state (like updating vital sign thresholds) even for offline devices; the state change requests are performed on the device shadow, and the device will sync to the shadow when it comes back online.

The edge devices may communicate directly with the AWS IoT Core 410 via Message Queue Telemetry Transport (MQTT) messages. Each type of data message may be published to a separate subject 416. One or more subscribers in the cloud can subscribe to each subject. This allows the system to evoke different Lambda functions 418 based on data type. Lambda functions can be automatically triggered to execute specific code by predetermined events like vital sign threshold crossings, changes in patient status, and data transmission. This allows the system to automate many functions, including sending alerts, updating databases, and sending reminders. AWS S3 420 is used to trigger the AWS Lambda 418 to immediately process incoming data after it is received over MQTT messages. There are separate Lambda functions which push data to a Postgres database (DB) 456, an object-relational database system. The Postgres DB 456 can be used to safely store and scale system uploaded datasets. Built on PostgreSQL, the DB was selected based on its strong reputation for reliability, data integrity, and fault tolerance. With PostgreSQL new data types (e.g. structured data types and documents) can be created and custom functions (e.g. query planning and optimization) can be built for the system 100. The Postgres DB 456 can serve as a system primary data store for system 100 web applications, patient time-series data, and machine learning models.

The Postgres DB 456 can be connected with an EC2 server 450, which provides secure and resizable cloud computing, as well as hosting a system Flask-based web app on a webserver 452. Each EC2 instance can perform all the functionalities of a traditional web server, with the added benefit of having flexibility to provision servers on demand based on the system's current computational requirements.

The EC2 server 450 can also run machine learning 458 on data stored in these databases. The system's machine learning block 458 allows the core network 110 to embed machine learning processing directly into system 100 SQL queries as calls to functions. This also allows for training and deploying system 100 models faster by leveraging the compute power of ML-optimized cloud servers. In addition to developer generated patient-oriented models like heart failure prediction and classification, the block 458 can access off-the-shelf machine learning algorithms and services from AWS. An example is Amazon SageMaker, which can help to automate the exploration of new and improved models by using its built-in tools which automatically build, train, and tune machine learning models.

The system web app queries the Postgres DB 456 when populating information on the various pages. To integrate with various EMR and other health systems, the system uses their 3rd party APIs 440 to send and receive data between the system platform via an API engine 454 connected to the Postgres DB 456 and the platforms of the EMR and other health systems. This allows the system 100 to directly and securely inherit patient's medical records.

The specific API is dependent upon the particular third party, but each API allows for directly and securely inheriting patient's medical records. The patient's records may be parsed to initialize certain risk models for each patient, including open-source random forests trained to classify patients into risk category based on information in their medical records including age, sex, and history of smoking. System internal APIs are maintained and secured in the system API engine 454, which can perform functions such as calling SQL queries and interacting with third party APIs 440. Examples of system 100 APIs include message brokers that provide interoperability between the system web application, internal databases, and 3rd party APIs.

The edge devices 130, 150 can provide health management from prevention and early diagnosis to chronic disease management to saving life by making an action in real time by integration and (decision making) perception capability. The edge enables and integrates this health management service as part of daily life, and this service can lower rising health care costs. Senior people can enjoy their life in their home using this technology, and also patients discharged from a hospital do not need to get readmitted every few days.

The edge device allows for monitoring an individual and environment around him/her, analyzing a state of his/her health and adjusting medication, diet and entertainment to give the individual comfort with minimum effort from him/her or their family. The edge technology enables independent living in their home or in their suite as part of a senior community and reduces costs for family and Medicare.

Embodiments of the described technology describe how edge computing is used in the system 100, such as by applying artificial intelligence (AI) and machine learning at the edge to make the health management doable and cost effective at home and even in a car and around a city.

Figure 4C:
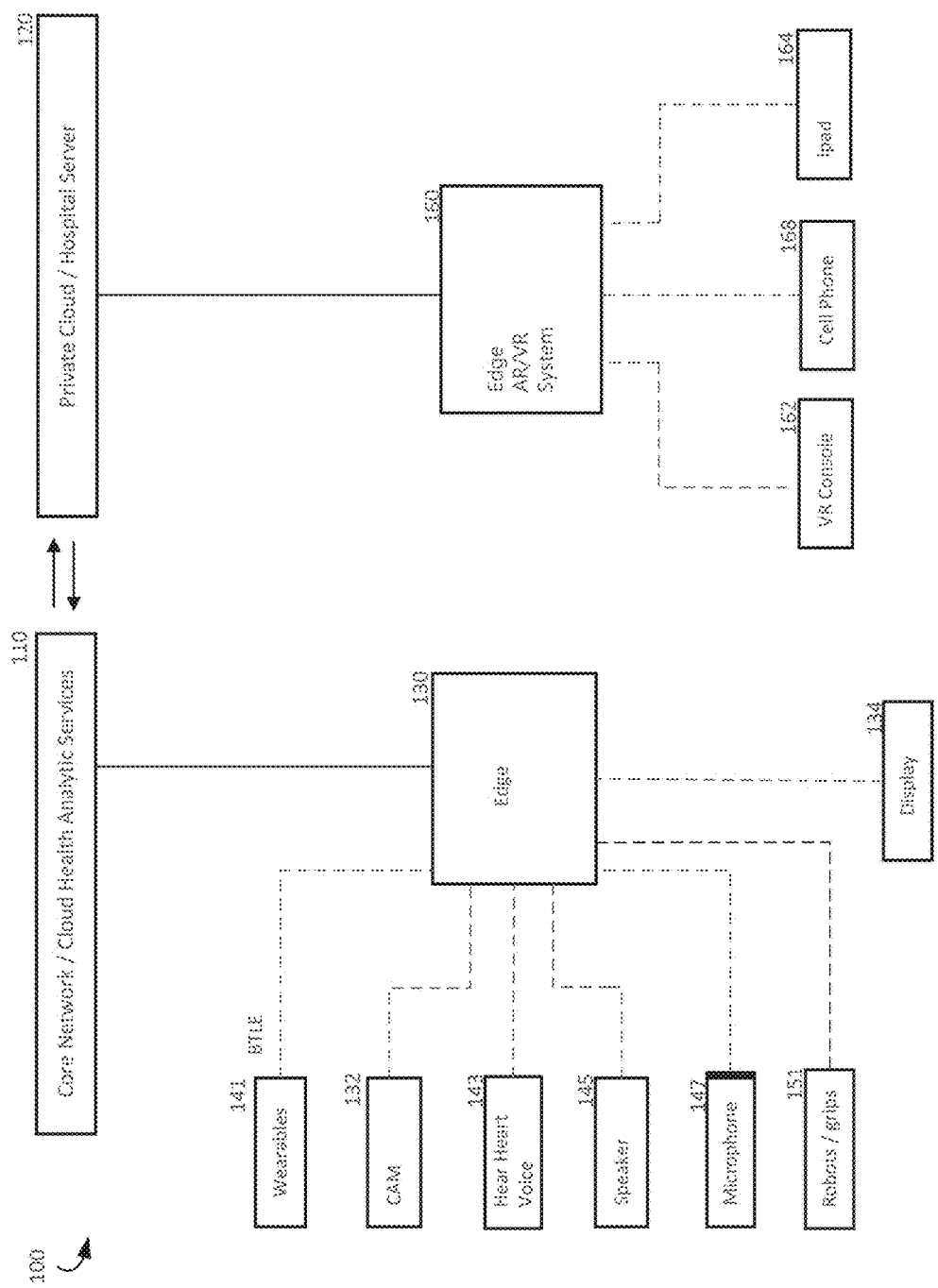
FIG. 4C is a high level block diagram of another embodiment of a system for decision making using distributed edge computing and machine learning.

FIG. 4C is a high level block diagram of another embodiment of a system for decision making using distributed edge computing and machine learning. For remote procedures, small surgery or even advanced telemedicine an edge to edge connection as shown in FIG. 4C taking advantage of a 5G core network and open radio access network (O-RAN) to achieve ultra low latency end-to-end and reliability that no other remote patient monitoring with AI solution currently offers. A physician and patient may feel they are present in a same room by the doctor looking at his/her mouth or ear via a camera 132 and listen to his heart 143 with interfaces that the edge provide as seen in FIG. 4C. A patient can leave messages for a nurse or doctor using the system speech recognition or care giver can control time of $SPO_2$ measurement using a personalized high accuracy speech recognition ML on the edge. In one embodiment, the system 100 can provide an automated orthostatic BP test where the edge talks with the patient and measures BP at two different positions, sitting and standing, (by using ML on accelerometer data it can recognize posture) and compare BP readings and send alarm if the difference is outside threshold set by a doctor. In certain embodiments, an interactive audio capability allows the edge system 130, 150 to discuss symptoms and feelings with patient using a speaker 145 and a microphone 147. The edge may then cross check answers with physiological signal measurements and detected events such as HRV<X or BP>Y or any kind of arrhythmia and make a comprehensive report to a doctor or nurse or care giver. Other interfaces include a BTLE interface with various wearables 141, and an interface for robots or grips 151. The edge system 160 can be connected to a VR console 162, a smartphone 160 and a tablet 164 (e.g., iPad). An edge box in a user's home or car or on the street pole can run one of the versions of the development's software algorithm to make sure of continuity of their health management service. Different features and configurations can be enabled and used in the version of software pushed from the core network 110 to an edge box at home versus an edge box at the street pole or in the car.

The edge can discover new paradigms in diagnosis and treatment follow-up using unsupervised learning on personal physiological signals while taking advantage of learned baselines from a bigger population in what is called evidence-based personalized medicine. The edge is a personal assistant to a patient and care giver including a doctor by bringing to their attention the discovered results from analyzing signals over time and letting the doctor make informed decisions, uncover the unknowns and the right personalized treatment.

The edge can have a user's diet information every day, for example, in a smart home setting from a refrigerator (such as using weight sensors and/or camera inside the refrigerator), physiological signals and the user's voice and face expression. The edge can discover a correlation between the user's health, physiological signals such as ECG and happiness with their diet, breathing, sleep and music listened to, such that the edge learns about the user and reinforces a good diet or favorite music to get good sleep, health and a happy mood. If the user's input quality degrades one day, as detected by a change in quality of diet or breathing or sleep for example, and their health condition degrades following that (such as an ECG irregularity), then the edge learns the weight of each input and can model their health condition, predict a future degradation of condition, determine the cause of problem and inform the user and their doctor to select the right treatment.

Cross correlation of any two (or a greater number of) signals measured over time such as heart rate, HRV (stress), blood pressure, oxygen saturation level, respiration rate, physical activity (type and step count), sleep quality and heart rhythm (ECG) irregularity (arrhythmia percentage over time), and finding multiple unique correlation patterns that can be shown to have been repeated in a person, and using these features to predict CHF (a composite risk score or binary prediction), and treating the issue before resulting in heart failure is desired. Discovering these physiological signal changes few hours before shortness of breath and other symptoms of HF happen that can indicate a risk factor for heart failure and reporting the risk level to a physician can be done. Personalized medicine and evidence-based diagnosis can happen by using edge technology, thereby reducing risk and mistakes due to trial and error treatment and a lack of right diagnosis.

This system 100 and service can function as a health advisor to any person and as an assistant to a doctor. Because heart arrhythmias are complex and may have underlying or contributing causes related to lifestyle choices, the developer is uncovering these previously unknown underlying or contributing causes by using a correlation neural network scheme so as to help doctors to address their patients' health needs.

Figure 2:
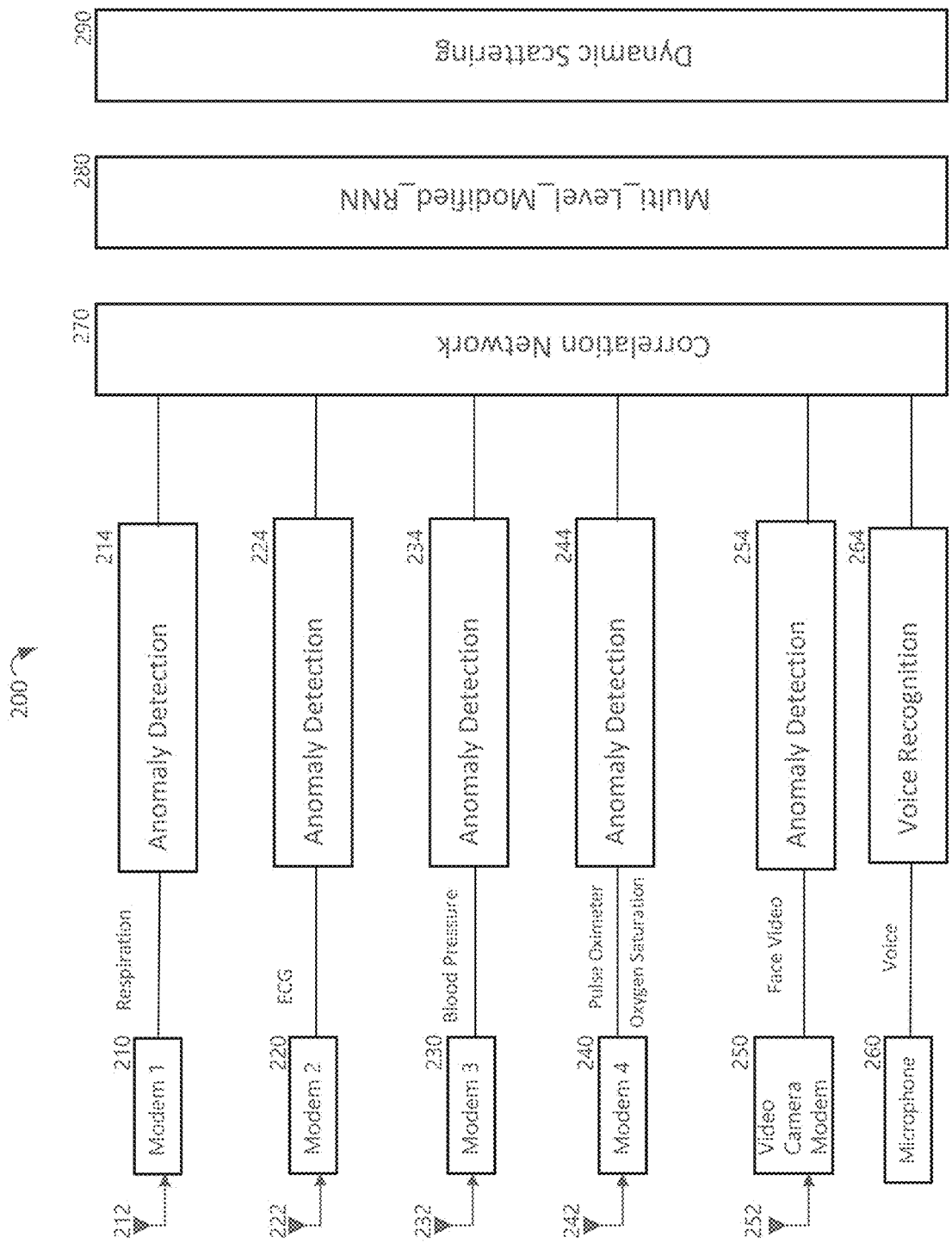
FIG. 2 is a block diagram of an embodiment for processing human physiological signals such as performed on the system of FIG. 1.

FIG. 2 is a block diagram of a system 200 for processing human physiological signals such as performed on the system of FIG. 1. In some embodiments, a data set in the cloud 110 is used to do supervised machine learning in the cloud and downloads parameters to the edge system 130, 150. Then, the described technology may continue with feed forward (FF) detection for face expression and unsupervised machine learning and correlation discovery for evidence based and personalized medicine shown in FIG. 2.

Referring to FIG. 2, wireless modems 210, 220, 230, 240 receive different signals 212, 222, 232, 242 such as ECG, BP, SPO2 and accelerometers from sensory devices 144, 148 located on patient 140 as shown in FIG. 1. The system 200 may also include a video camera modem 250 that receives a patient's face image and provides the face video to the anomaly detection block 254, and a microphone 260 that provides a patient's voice to a voice recognition block 264. Preprocessing and anomaly detection blocks or modules 214, 224, 234, 244, 254 are performed on these signals. As described in FIG. 9 and FIG. 10 hereinbelow, at least one of the anomaly detection modules 214, 224, 234, 244, and 254 may be realized with or include, for example, threshold detectors 920, 1020 or arrhythmia detectors 910, 1010 using classification on ECG or low activity detection using random forest and attention classification 922, 1022 on accelerometers data. The output of the anomaly detection modules 214, 224, 234, 244, 254 are fed to a correlation network 270 to determine correlations between signals including, but not limited to, HR, HRV, arrhythmia, BP, $SPO_2$, and activity described in the description of FIG. 3. A multi-level modified RNN (MLM RNN) block 280 may include a bank of Recurrent Neural Networks (RNNs) that has interactions with each other based on two features described in detail in conjunction with FIG. 3. The decision making block 290 has been described in detail at FIG. 3, and in one embodiment it could perform dynamic scattering as described at FIG. 3.

In some embodiments, the described technology covers algorithms and methods to detect bio-signals dependencies as some bio-markers can be used for prevention, early diagnosis and treatment (precision medicine).

Figure 9:
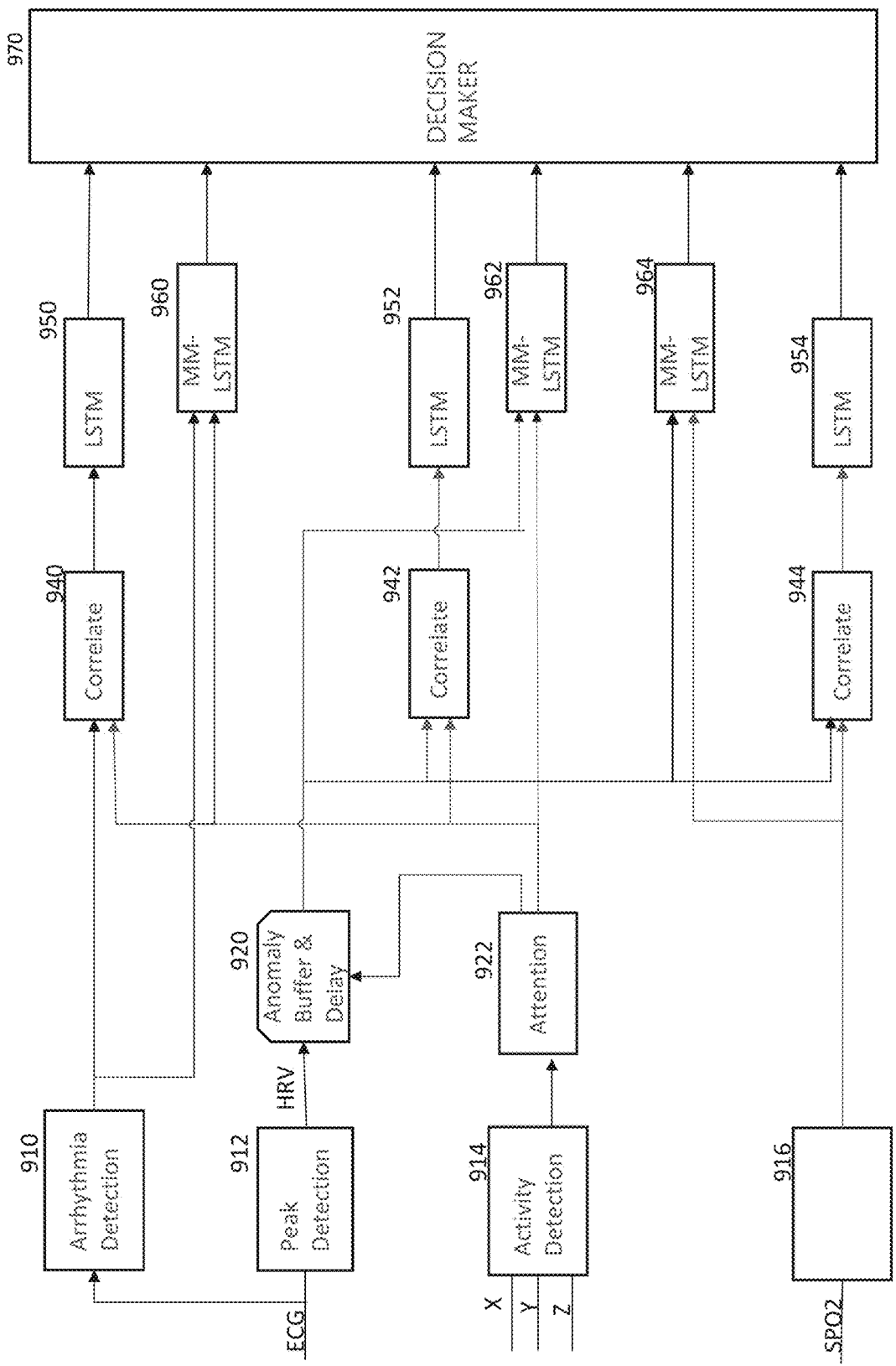
FIG. 9 is a block diagram of another embodiment for processing human physiological signals through decision making such as performed on the system of FIG. 1.

In some embodiments, the system 100 detects when a patient's vital signs deteriorate (anomaly detection), for example, by using threshold detectors, or a modified attention network, or arrhythmia detection as described in conjunction with FIG. 9. The anomaly detection blocks (920, 922) function as a switch that starts a sequence of events when the input signal is determined to cross a certain threshold. Examples may include, but are not limited to, resting heart rate above about 100 bpm, $SpO_2$ falling below about 85% or a decrease in $SpO_2$ by more than about 10 points in a short time.

Figure 3:
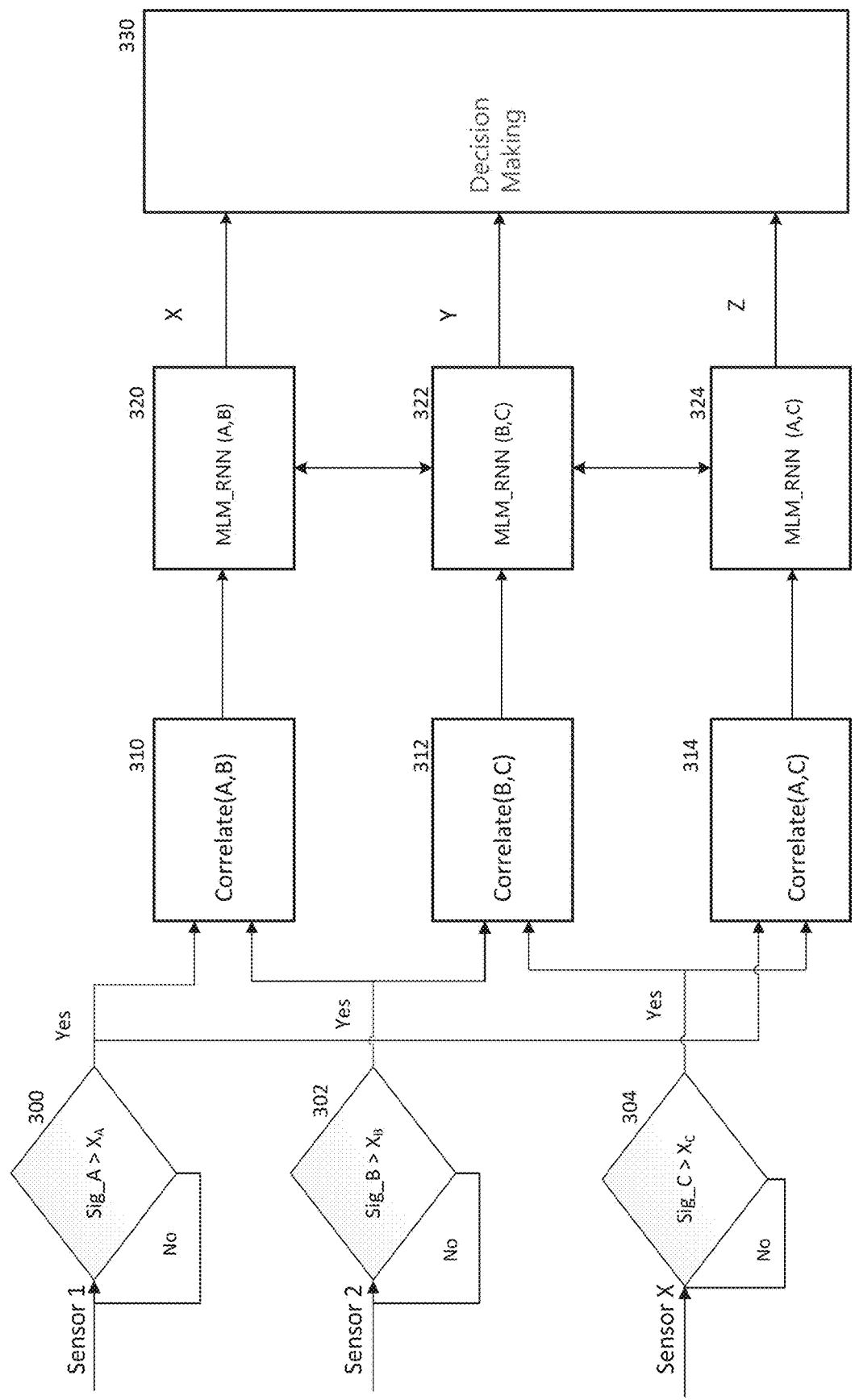
FIG. 3 is a block diagram of an embodiment for processing human physiological signals through decision making such as performed on the system of FIG. 1.

Referring to FIG. 3, inputs for anomaly detection blocks 300, 302, 304 can include raw or processed data (including extracted features, such as heart rate) coming from sensor 1 to sensor x such as those described with respect to FIG. 1. Although FIG. 3 shows three anomaly detection blocks and three sensors, in some embodiments, two sensors or more than three sensors can be used. When a bio-potential signal A (Sig_A) such as heart rate passes a certain (first) threshold ($X_A$) and stays there (high/low) for more than about a few minutes, it can be tagged as an event, e.g., "activity A". Then monitoring of other signals such as blood pressure, respiration rate, activity, facial expression and voice can be performed to determine if any other abnormal activity follows activity A and shows a consistent correlation.

When a bio-potential signal B (Sig_B) passes beyond a normal range or a second threshold (or normal expression) ($X_B$), the correlation blocks or modules 310, 312, 314 can start correlation operations and measure cross correlation of stored activity with new activity (which can have a lag) in real time. If a correlation value passes a certain threshold, a next neural network goes to a new state, increments a risk factor based on a correlation peak between heart rate and systolic blood pressure, for example, and detects a time interval that this correlation value stays up (active). The edge can record signal B activity and a correlation of signal A and signal B activities. The system and method can measure a lag time interval between these two activities or any other subsequent activities and can look for discovering a pattern that repeats itself for this individual.

In certain embodiments, every time both activity A and activity B happen, the correlation network can generate correlation values as a function of time while two time series of signal A and signal B can be presented as inputs to the network. As shown in FIG. 3, a correlation neural network is triggered to perform computation of these correlations between every pair of inputs when abnormal events happen in both inputs to the correlation blocks 310, 312, 314, and it also computes lag between the two abnormal events based on a synchronized time stamp in the edge system.

Correlation may be implemented by Equation 1:

$$C(n) = \sum_{m=n-w+1}^{n} A_{(m-k)} B_{(m)} \qquad \text{Equation 1}$$

where
A=signal A,
B=signal B,
m=time index for summation over window of time w,
n=time index for output of correlation,
w=length of window to compute correlation, and
k=lag parameter between two signals.

Certain embodiments compute a correlation for any lag value when anomaly detection is not utilized.

The above equation is merely an example equation and other equations may also be used. The correlation blocks 310, 312, 314 can provide two useful pieces of information: an amount of correlation between the two signals as a function of lag time, and the lag associated with time of maximum correlation. The lag is represented by the time difference between signal A and signal B passing their respective thresholds.

Correlation can be computed over a time window w that can be dynamically set based on lag and anomaly detection thresholds and a length of time that input A and B signals stay above the thresholds. In one embodiment, the w can be a hyperparameter that can be selected by training on outputs of correlations for a given objective such as risk assessment of acute heart failure. The time window can be the shortest of an activity A window and an activity B window (period that each signal/activity stays above threshold). Anomaly detection thresholds and correlation thresholds can be learned for a given disease or for a given individual.

Figure 20:
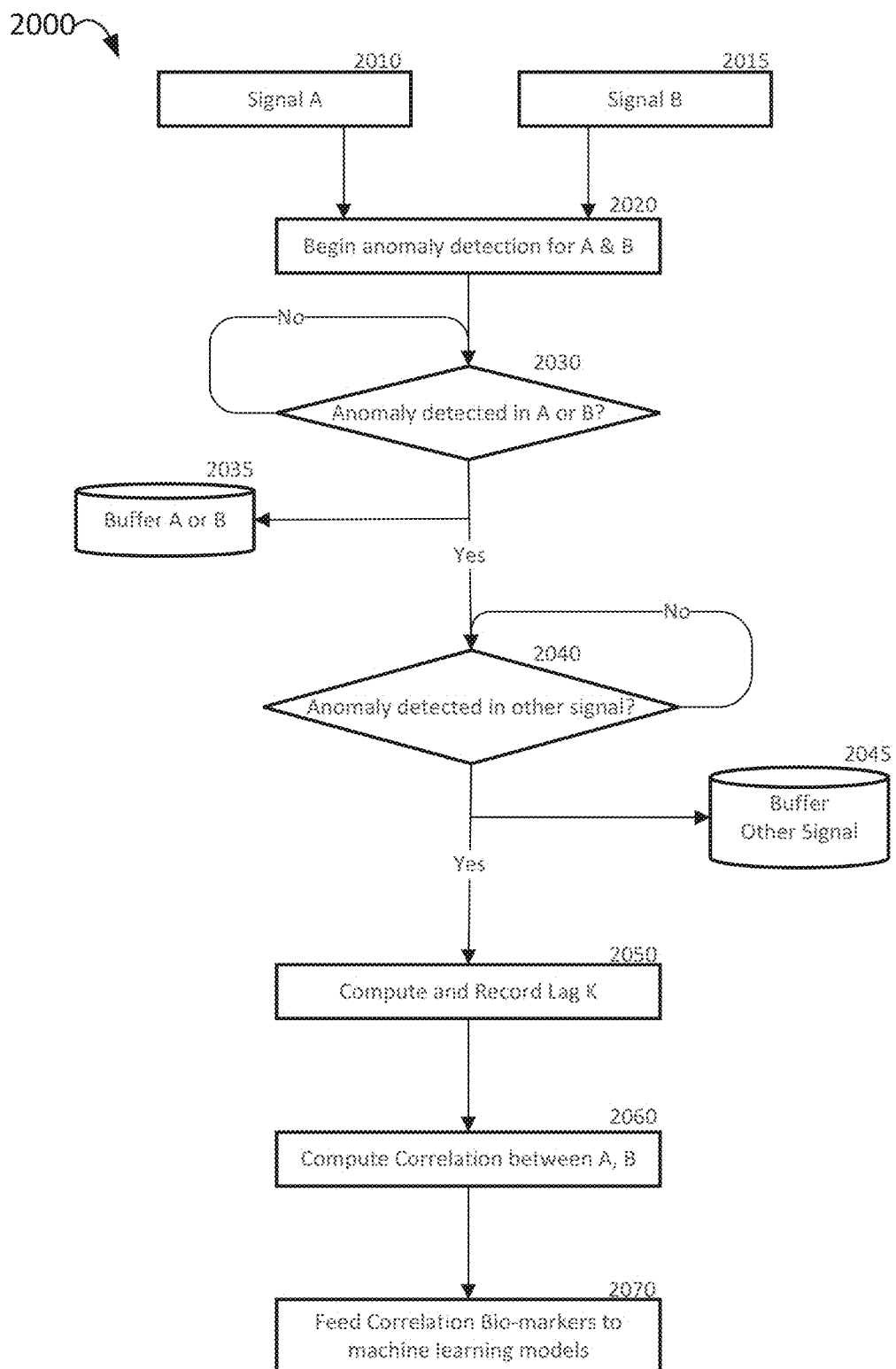
FIG. 20 is a flowchart of an embodiment of an example flow for processing two human physiological signals.

FIG. 20 is a flowchart that depicts a process 2000 of a particular configuration of anomaly detection blocks. Although the process 2000 is described herein with reference to a particular order, in various embodiments, states herein may be performed in a different order, or omitted, and additional states may be added. This may apply to the other flowcharts in the figures. These blocks are constantly processing their input signals to detect anomalies. In a step 2020, anomaly detection for signal A 2010 or signal B 2015 begins. When a biopotential signal A 2010 such as heart rate passes a certain threshold, and stays there (high/low) for more than about a few minutes, it can be tagged as an anomaly or event, e.g., "activity A". This anomaly is detected at a decision step 2030. After that step, a buffer 2035 begins to fill with samples of the signal in which the anomaly was detected. The other signal, in this case signal B 2015, continues to be monitored for anomalies. If an anomaly is detected in this signal, at a decision step 2040, it triggers a separate buffer 2045 to begin filling with samples. The lag "k" or, in other words, time difference between the anomaly event detections is recorded at step 2050. Next, the cross-correlation of the A and B signals for lag "k" is computed at a step 2060 based on, for example, the equation 1 above. These correlation bio-markers are then fed 2070 to the machine learning models described in different embodiments herein.

A correlation network is a kind of dynamic feature computation from more than one signal which triggers a next stage of system machine learning that could be an interconnected multi-level modified recurrent neural network (RNN) 330, 332, 334.

Events that arrived at the edge system can be synchronized based on receiving a time adjusted response from every device to a unique beacon transmitted from the edge.

RNNs are a class of neural networks specialized for processing sequential data, such as time-series. These networks can scale to long sequences, and can process sequences of variable length. RNNs can start with some initialized state, and then operate by iterating over an input sequence. At each time-step of the sequence, they combine the current sequence element with the output from the previous time-step, and perform computation on this value to produce the next output.

The correlation networks 310, 312, 314 (see FIG. 3), plus a multi-level modified recurrent neural network (MLM-RNN) including an MLM-LSTM, can determine whether correlation between activity A, activity B and activity C are consistent, a same pattern repeats over time and the lags between these physiological signal changes are unique for a given person.

There are many inputs or factors that can be narrowed down to a few main factors that cause a problem, such as a high oxygen demand vs oxygen supply, low activity, weak cardiac output and consequently acute heart failure.

Figure 23:
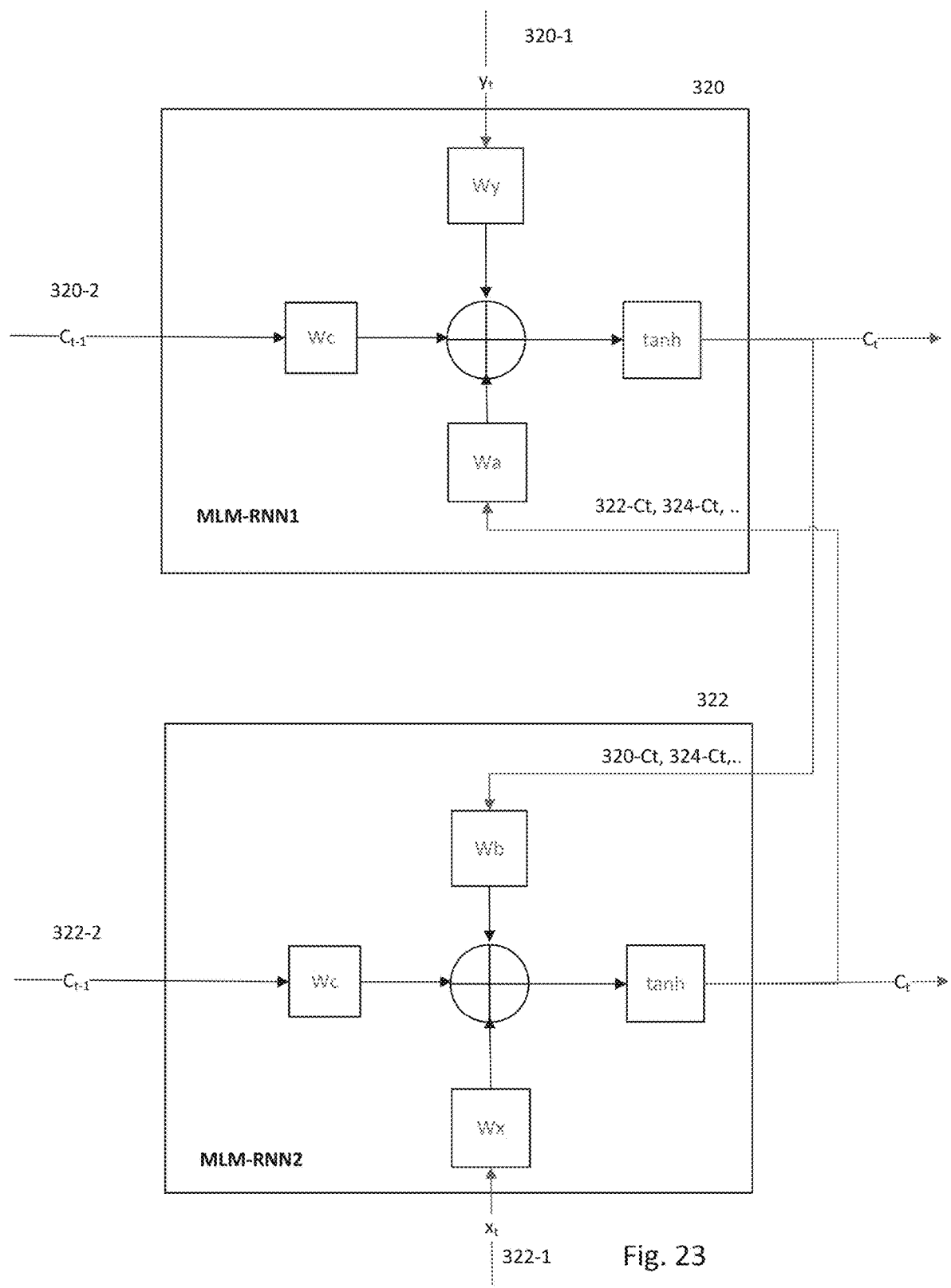
FIG. 23 is a block diagram of an embodiment for a portion of an example multi-level modified (MLM) recurrent neural network (RNN) illustrating an example way to combine information including hidden states between separate RNNs.

FIG. 23 is a block diagram of an embodiment for a portion of an example multi-level modified (MLM) recurrent neural network (RNN) illustrating an example way to combine information including hidden states between separate RNNs. To find a relationship among correlations between activities A, B, and C, the edge system can combine information from the separate MLM-RNNs 320, 322, 324. This combination of information is represented by the vertical arrows between the MLM-RNNs (see also FIG. 3). One way to combine information is to use a mutual exchange of hidden states between each RNN cell. In this way, at each time step, all cells can receive the following as their input: the next output of the cross-correlation signal 320-1; their own previous output 320-2; and the output from the other RNNs (322-Ct, 324-Ct and so forth) as depicted in the block diagram in FIG. 23. This diagram depicts a method for combining information between separate RNNs. As a base case, two RNNs are illustrated.

For each RNN, its previous cell state can be routed through Wc, a fully-connected neural network. Consider block 320 of FIG. 23 for example. The next output of the cross-correlation signal is multiplied by Wy, and cell states from other RNNs are multiplied through Wa. The outputs of all three neural network gates are summed before being passed through a tan h function to yield the new cell state Ct. This method can be extended to many RNNs. Each RNN can send its output Ct to all other RNNs, as well as to itself. For receiving multiple inputs from other RNNs, each RNN will concatenate these multiple Ct inputs into one vector, before passing it through its own gate Wa. For example, block 320 receives multiple inputs at its gate Wa, as indicated by the text "322-Ct, 324-Ct, . . . " on the arrow leading into Wa. This method of combining information can be used for combinations of signals with similar temporal dynamics. Since the cell states are shared between all RNNs, this method may provide the best performance when the input signals are varying along similar timescales.

A separate way to combine information from different RNNs is to have an observer that does computation on a collection of states across the separate RNNs. To achieve this, an N×T buffer of states can record the last T states from each of the N RNNs. This tensor of states can be processed by a separate neural architecture, e.g., an attention module as in 1050 of FIG. 10. This strategy, depicted in FIG. 18, can be used when there is a need to put attention on a long temporal history of multiple signals. In this method, an attention heatmap 1857 can be generated in two dimensions, across states and across signal types.

Figure 15:
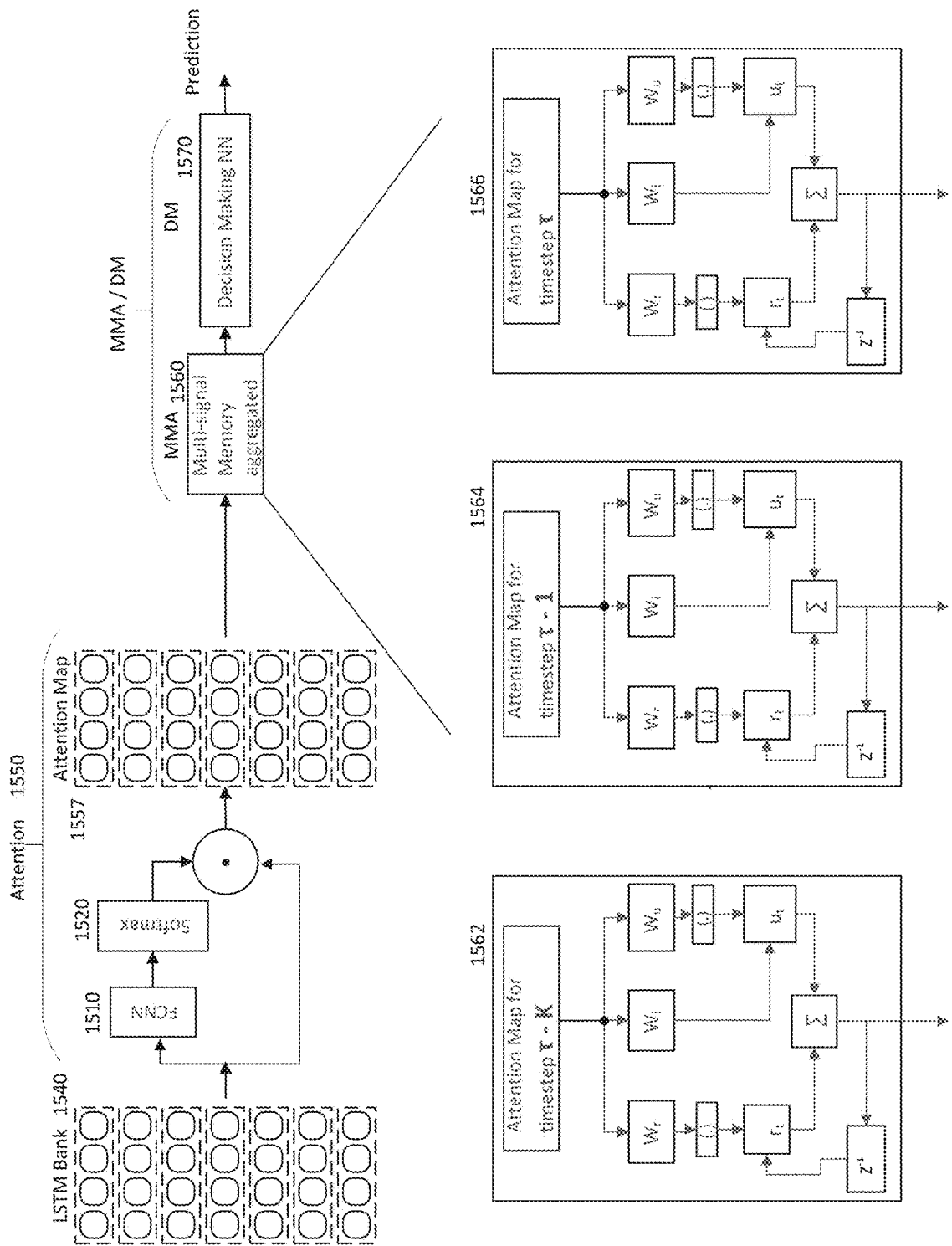
FIG. 15 is a block diagram of the example attention network and multi-signal memory aggregation in more detail.
Figure 16:
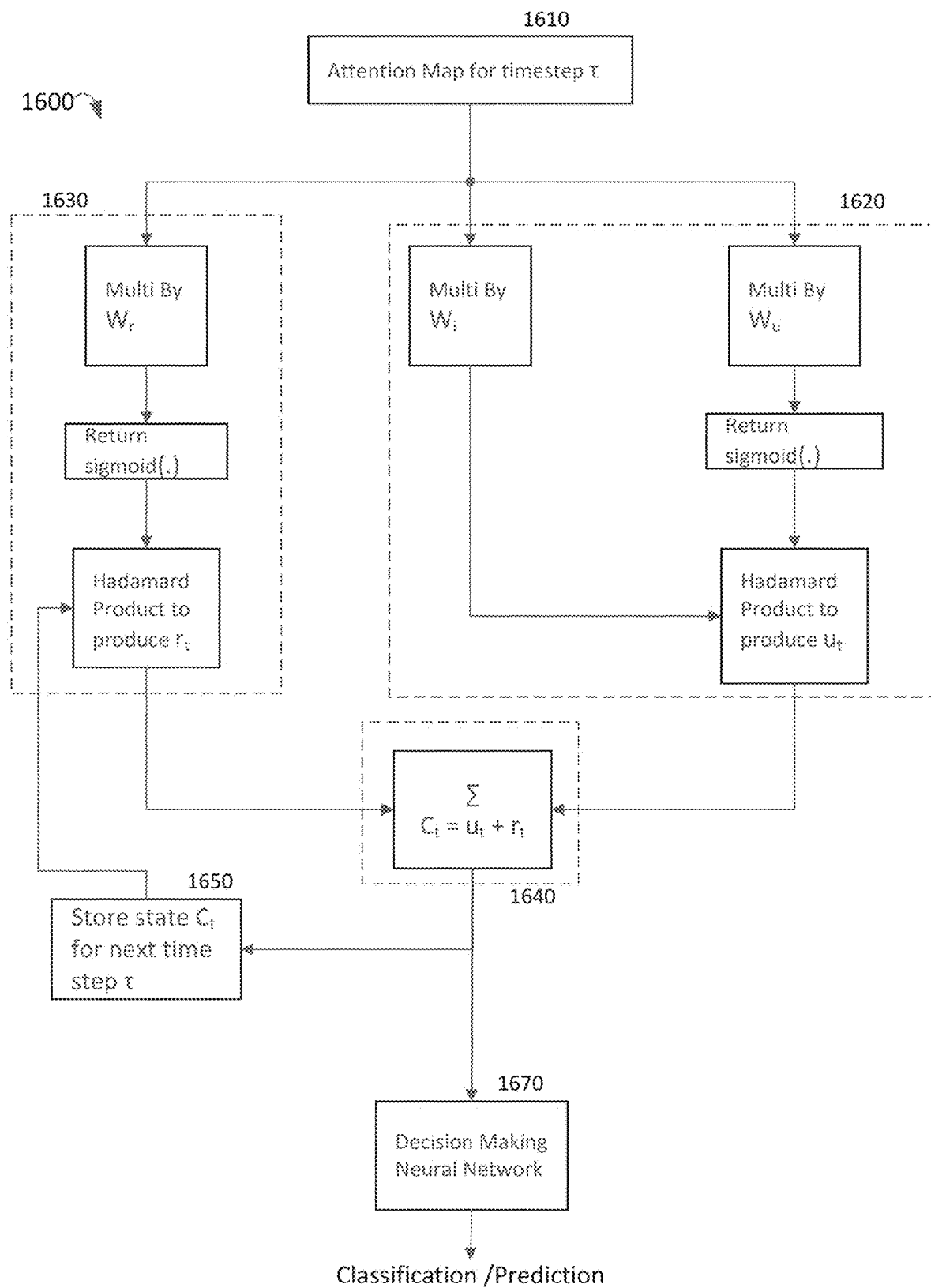
FIG. 16 is a block diagram of an example attention map at a particular time step and multi-signal memory aggregation in more detail.
Figure 18:
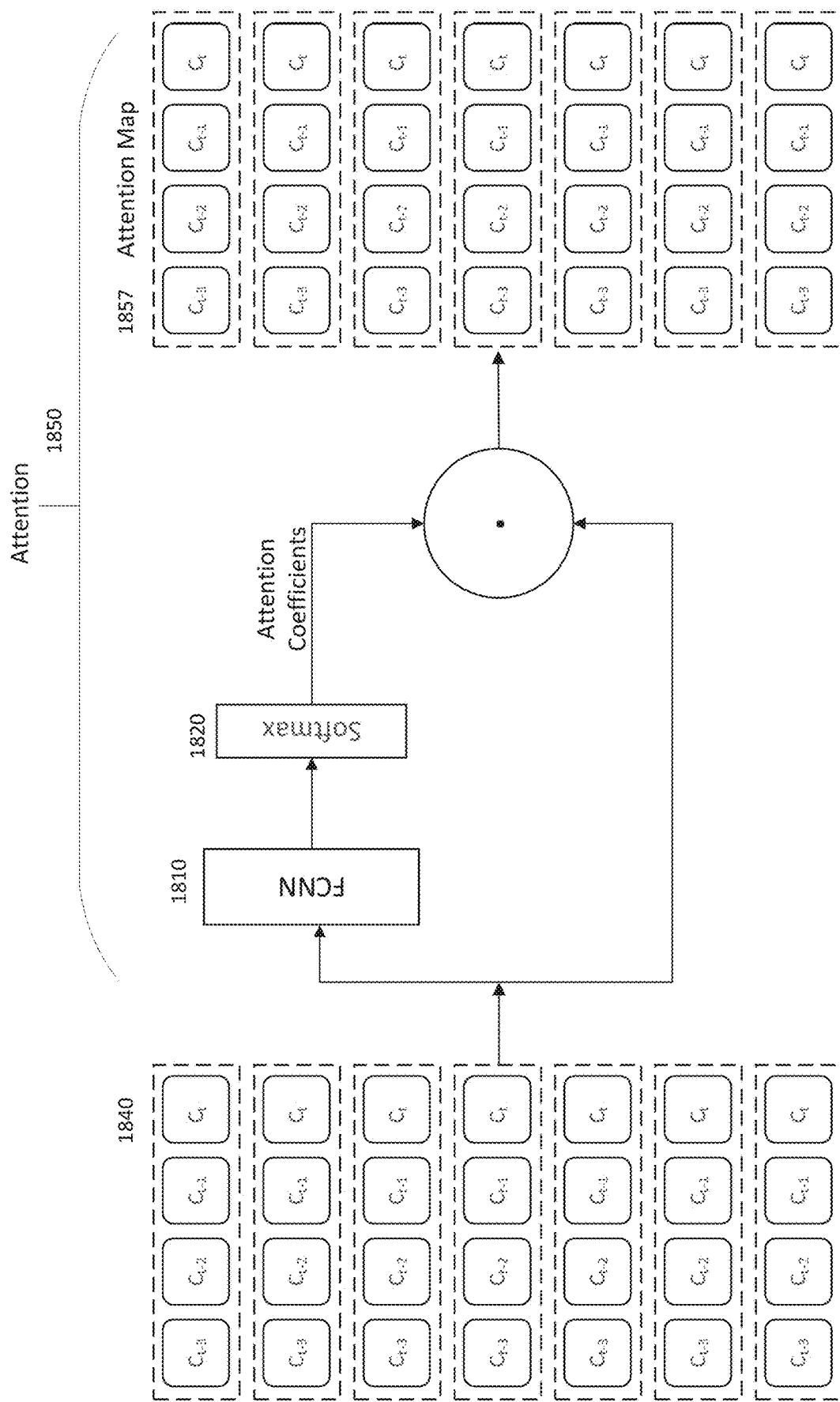
FIG. 18 is a block diagram illustrating an embodiment of generating an attention map using a fully connected neural network.

Referring to FIG. 18, the cell states from the bank 1840 of RNNs are buffered and passed into the attention network 1850, which finds interactions across the different signals and across states; these interactions are reflected in each of the two dimensions of its output. To compute the attention coefficients, the input sequence of signal states can be transformed into a matrix of scaling factors of the same shape as the input, by a fully connected neural network (FCNN) 1810 with Softmax activation 1820. This matrix represents the attention coefficients across signals and across states, effectively capturing interactions across both domains. This matrix is combined with the input states through element-wise multiplication to produce the attention map 1857. This modified attention layer can search over its input of time-locked mini-sequences from different signals and identify important patterns within subsets of these signal types. These patterns, encoded in the heat map, are then sent to a multi-memory aggregator (such as shown in FIGS. 15 and 16) to maintain a longer temporal history. The attention module also provides better interpretability through its heatmap.

The activity A time window could be a different length than the activity B time window and can be different for different people. Normalizing different activity can be done since each signal can be produced in different system with a different dynamic.

Correlating a person's activity with his/her high heart rate, high blood pressure, and shortness of breath can be performed. This development also covers how these correlation values over time help predict risk factor and stages of heart failure a person can be expected to experience if not followed up with a doctor. This development describes a new multi-level modified RNN realization that can learn risk factors and predict possible heart failure based on all correlation patterns.

Signals of patients that have been diagnosed with different stages of heart failure have been measured and multiple correlation time series (curves) have been computed. They can be presented simultaneously as inputs to the interconnected multi-level modified RNN architecture that sends their outputs to the decision-making block 330 shown in FIG. 3.

The system 100 can use the outputs of the interconnected multi-level modified RNNs to map patients to a stage of heart failure they belong to based on correlation patterns, features derived from them, and risk factors learned in neural networks according to heart failure guidelines. For example, correlation of cardiac output and shortness of breath with activity of patient can be used to differentiate a congestive heart failure (CHF) patient from an athlete. One layer that can perform this kind of classification is the softmax layer 1820 as shown in FIG. 18, whose output represents the probability of the input data belonging to each of the four heart failure classes defined by the New York Heart Association.

FIG. 17A is a block diagram of an embodiment of decision making that outputs a scalar. FIG. 17B is a block diagram of an embodiment of decision making that outputs a binary decision. FIG. 17C is a block diagram of an embodiment of decision making that outputs a multi-class decision. In one embodiment, the decision making block 330 performs a classification decision, such as heart failure classification. This decision making can take three different forms, as described in FIGS. 17A-17C.

The three forms may include: 1) a positive scalar for risk assessment (to quantify a risk score between zero and 100, for example) as shown in FIG. 17A; 2) a binary format for prediction (yes/no) as shown in FIG. 17B; or 3) a multi-class format for multi-class classification (heart failure classes A, B, C, D) as shown in FIG. 17C. In all three cases, an input 1710, 1720, 1730 of size 1×D can be passed through a one-layer fully connected neural network 1712, 1722, 1732 with weights of size D×k for k classes (for a positive scalar, k=1); the output 1714, 1724, 1734, then, will be of shape 1×k. The differences between these three approaches are as follows. For risk assessment in FIG. 17A, k=1, and so the output will be of size 1×1. This raw value can be used as the decision. For binary prediction in FIG. 17B, the output can be of size 1×2. The decision will be made from this array by using an Argmax function 1726, which returns the index of the maximum element in the array. So an output consisting of [0.3, 0.7] will return 2 for the decision, since the maximum element occupies index 2. Multi-class classification in FIG. 17C is similar to binary classification, where k can be any integer greater than 2, and an Argmax function 1736 is used to make the decision. Different decisions can be made simultaneously by feeding the multi-signal memory output in parallel through several different layers. The decision-making block can be used to train the full system end-to-end. After training is complete in the cloud 110, the parameters and models can be used to reconfigure the edge system 130, 150.

In another embodiment, the decision making block can perform scattering on the outputs of the MLM-RNNs. Scattering is the problem of dividing a set of data so that patients within each division are more similar to each other than to those in other divisions. Using a combination of multiple bio-signals and sensor types may increase discriminative power of a scattering algorithm. In one embodiment, as shown in FIG. 3, pre-trained RNNs 320, 322, 324 can be used to dynamically scatter their cross-correlation inputs to make these graphs. This allows each patient to occupy a different region of parameter space at different points in time; alerts can be set if the patient is detected to be in a different subspace of parameter space for some period of time, based on the recent and current scattered input.

A selection of three variables can be scattered to make interpretable graphs for clinicians and patients to review. By storing the dynamic scattering across time, animations can be used to illustrate patient progress or deterioration across time.

In one example, heart failure patients may be distinguished from healthy controls by scattering blood pressure, activity, heart rate, and HRV. Heart failure patients are more likely to have high blood pressure and lower HRV compared with controls. They are likely to have a higher heart rate during periods of low to moderate activity, due to their heart working harder to increase its effective output. In this example, RNN 320 can take correlation output from blood pressure and HRV. Similarly, RNN 322 can take correlation output from heart rate and activity. These two correlations can be scattered to distinguish healthy vs. heart failure patients.

In one embodiment, the system 100 can take output of the RNN as shown in FIG. 3, without cross-talk between cell states of the separate RNNs. In another embodiment, the system 100 can take output of the RNN as shown in FIG. 3 with cross-talk between cell states (as explained in FIG. 23). This allows the RNNs to share information with each other in order to increase their utility as input for the scattering algorithm. In some embodiments, this can be conceptualized by treating the series of matrix multiplications inside FIG. 23 as multiple linear transformations, which can function to project the input data into more easily separable subspaces.

A few specific examples of what types of decisions can be made in the decision making block 330:

1) Binary output as prediction of high probability of adverse event, such as acute heart failure.

2) Risk Score, a number between 1 and 100 that quantifies the patient's current overall risk. This prediction is made by passing through a 1-unit neural network with scaled sigmoid activation function.

3) Heart Failure Classification (NYHA): The New York Heart Association divides heart failure into four classes: Class 1, 2, 3, and 4, based on level of activity and presence of other symptoms. Routing the multi-signal memory through a fully-connected layer with four units (one for each class) and Softmax activation can predict the classification. The output of Softmax represents the probability of the input data belonging to each class.

4) Heart Failure Classification (ACC): The American Heart Association and the American College of Cardiology have developed classification types A, B, C, and D based on structural heart disease and presence of heart failure symptoms. Routing the Multi-signal memory through a fully-connected layer with four units (one for each class) and Softmax activation can predict the classification. The output of Softmax represents the probability of the input data belonging to each class.

5) Heart-failure subtypes: Softmax activation over N classes a) As another objective, a separate model(s) can be trained to classify the patient into one of several sub-types of heart-failure. These include reduced vs. preserved ejection fraction.

b) An alternative model can be trained to distinguish between left-sided and right-sided heart failure, and identify congestive heart failure.

Then in the edge, the parameters of a pretrained interconnected neural network can be optimized in real time with semi-supervised learning schemes Additionally, teams of trained clinicians can help to provide annotations on data from each patient in order to fine-tune and personalize each patient's own machine learning models.

In some embodiments, Equation 2 shown below provides a high correlation of heart rate (HR) and systolic blood pressure (BP) detected in real time on the edge to manifest oxygen demand exceeding oxygen supply and it can predict myocardial ischemia or myocardial infarction especially when it has correlation with reduced activity.

$$C(n) = \sum_{m=n-w+1}^{n} HR_{(m-k)} SBP_{(m)} \qquad \text{Equation 2}$$

where 'w' is the shorter time window for the two activities that have passed their corresponding thresholds and have triggered execution of correlation between the two.

Some risk factors that are genetic risk factors plus environmental risk factors accumulated over time are quantified. These bio-markers can be discovered for different genetic pools. If one has some genetic data from some patients and can correlate some of these bio-markers with genetic data, then one can establish a reference data set and parameters of a neural network model that helps to predict that people with those bio-markers may have genetic background of a given disease. The system and method can suggest to a patient (insurance) to take genetic testing to confirm diagnosis and start a right treatment early on.

Discovering these bio-signals dependency patterns gives new insights to doctors that helps not only early diagnosis of existing diseases, and narrowing down and identifying a source, but also discovering new diseases and selecting a right treatment plan based on quantitative patterns of data (evidence-based medicine and precision medicine and personalized medicine).

The system 100 in FIG. 1 and FIG. 4C is capable of facilitating biofeedback. Detecting dependency patterns of a user's mood and heart rate and sensing the mood and commanding to a multi-media center to play music and/or play a video that regulates the user's mood and sense and feedback to a controller (multi-media player) to feed right input to our sensory modality (ear, eye) can be performed. If this control loop is closed, the system and method can be used to help the user's heart rate to come down, avoid burning out the heart muscles and eventually heart failure or heart attack.

In certain embodiments, each disease/condition can be configured using an efficiently designed multi-level correlation algorithm in a network that specializes in a self-configured multi-level interconnected modified RNN as multiple measured time series are presented to the network in real time. One embodiment could be a hardware realization to get the best speed and power consumption for a health management application of the edge technology such as the prediction of Acute Heart Failure.

In some embodiments, the system 100 takes as its input one or more measurable bio-signals from wearable or implanted sensors. These bio-signals may include, but are not limited to: ECG, activity, blood pressure, $SpO_2$, respiration, bioimpedance, and body weight.

A variety of algorithms allow the edge to provide remote patient monitoring combined with personalized medicine. This includes adverse event detection and prediction.

Multi-Modality

There are different kinds of recurrent neural networks (RNNs) 320, 322, 324 as described with respect to FIG. 3. One kind of RNN called long short term memory (LSTM) is modified in two forms as described following:

In one embodiment, by modifying the LSTM to allow two input sources, each having a different sampling time, a multi-modal LSTM (MM-LSTM) was developed. This approach is described in conjunction with FIG. 9 and FIG. 21.

Another embodiment is implemented by applying each input from a given source (or derived features) to a single LSTM within a bank of LSTMs, and then applying attention on states of a multi-level LSTM (MLM-LSTM). This MLM-LSTM encompasses a bank of LSTMs. This approach is described in conjunction with FIG. 10 and FIG. 15 (FIGS. 11, 12, 13 and 14 depict different embodiments of MLM-LSTM).

Figure 5:
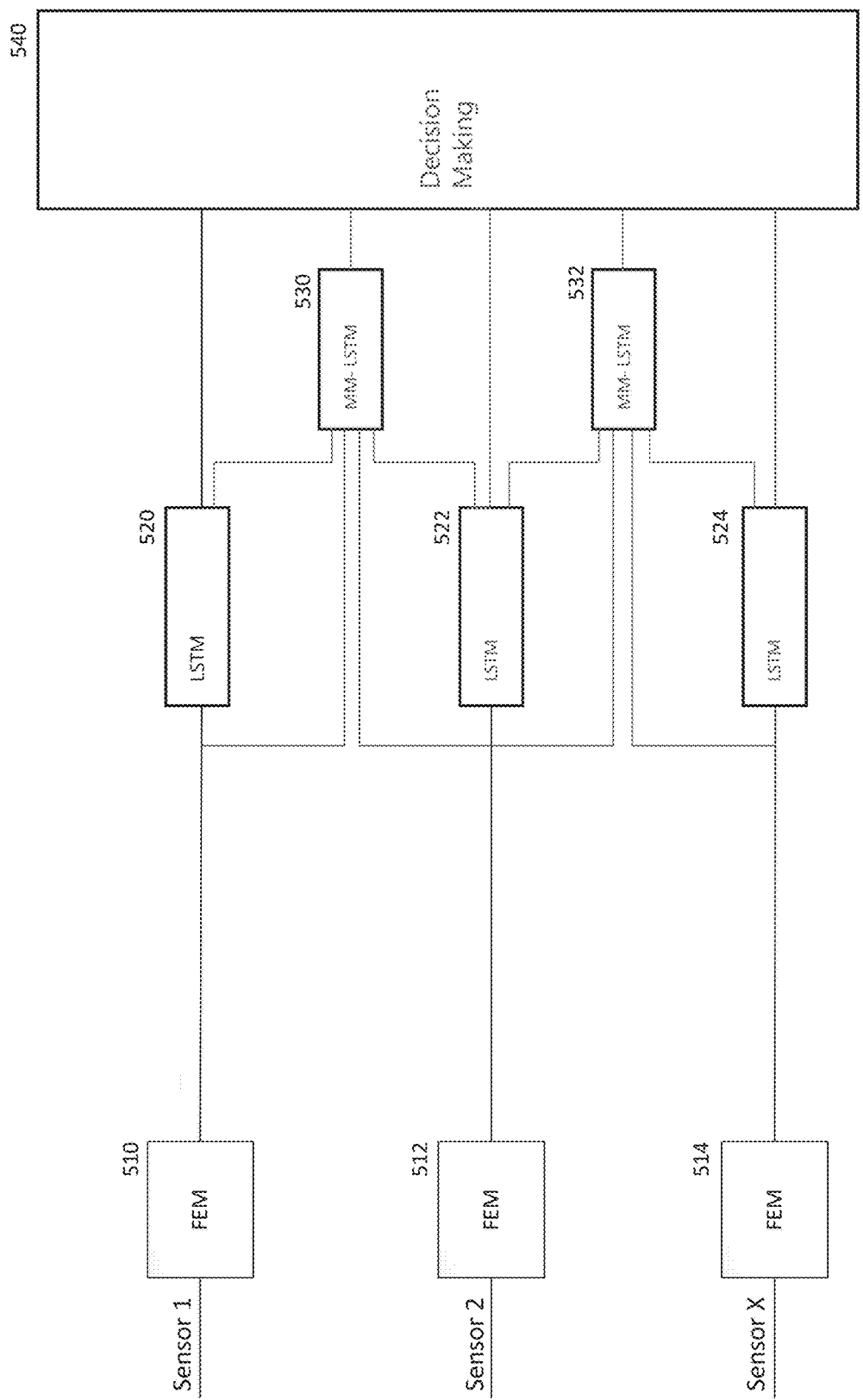
FIG. 5 is a block diagram of another embodiment for processing human physiological signals through decision making such as performed on the system of FIG. 1.

FIG. 5 is a block diagram of another embodiment for processing human physiological signals through decision making such as performed on the system of FIG. 1. Inside the edge system 130, 150, features can be extracted from multiple sensors as shown in FIG. 5. Feature extraction subsystems 510, 512, 514 compute features from sensory signals as shown in the figure.

In FIG. 5, features can be extracted from various sensors. These features are passed into various blocks, whose outputs are integrated by a decision maker 540. In one embodiment of the multi-level modified deep learning approach shown in FIG. 5, derived features first go through sub-blocks such as a LSTM 520, 522, 524. In this embodiment, these may be "vanilla" LSTMs.

LSTMs provide an improvement over traditional "vanilla" recurrent neural networks by allowing continuous regulation of the cell memory through various gates. It also helps mitigate the problems of vanishing and exploding gradients during back-propagation.

LSTM Gates

Let:
$h_{t-1}$=previous hidden state
$W_g$=recurrent matrix through gate g
$b_g$=bias through gate g Forgetting Gate:

$$f_t(x) = \sigma(W_f[h_{t-1}, x_t] + b_f) \qquad \text{i.}$$

Input Gate:

$$i_t(x) = \sigma(W_i[h_{t-1}, x_t] + b_i) \qquad \text{i.}$$

Tan h Layer:

$$\tilde{C}_t = \tan h(W_C[h_{t-1}, x_t] + b_c) \qquad \text{i.}$$

Output Gate:

$$o_t(x) = \sigma(W_o[h_{t-1}, x_t] + b_o) \qquad \text{i.}$$

The Tan h layer merges the two paths into a shared cell state.

The derived features are passed into a first LSTM to learn patterns from each of sensor features and then go through another MM-LSTM 530, 532 (as described below) to learn patterns on combination of two or more sensors' features (530), plus inputs from the state of the first group of LSTMs.

The output of first group of LSTMs and the second group of LSTMs are combined in a late fusion block that performs decision making (540). To combine the output of all previous LSTMs into one input, the output state vectors from each LSTM can simply be concatenated into a longer vector. This vector can then be passed through a single fully-connected layer to make a decision. Different kinds of decisions are shown in FIG. 17.

The complete description of decision making blocks are described above as part of FIG. 3 description. A brief description is provided below.

This decision maker 540 can also take as its input a group of predictions in order to decide based on a weighted vote count, or other features such as transformed time-series data which is mapped through a Softmax function to a predicted class (this can give a probability of belonging to class 2 or class 3 heart failure, based on data of last twelve hours or last one hundred twenty states in the LSTM bank).

To perform vote counting, the previous layers (520, 522, 524, 530, 532) may use, e.g., a Softmax layer to map their output directly to a prediction. Then the decision maker 540 can hold a vote over these decisions to determine the majority, and report the majority as its decision.

For risk assessment, the previous layers can compute a scalar output, and the decision making block 540 can return a weighted average as the final quantification of risk.

Multi-Modal LSTM (MM-LSTM)

The MM-LSTM can incorporate two or more inputs from different modalities. In one embodiment, two separate paths are used for each modality of incoming data and each modality is treated with different weight matrices.

Let:

$u_t = [x_t; y_t]$.

$h_{t-1}^x$ = previous hidden state for x
$h_{t-1}^y$ = previous hidden state for y
$W_{g,x}$ = recurrent matrix for x through gate g
$b_{g,i}$ = bias for x through gate g The two separate paths are routed through the following junctions:

Forgetting Gates:

$f_t(x) = \sigma(W_{f,x}[h_{t-1}^x, x_t] + b_{f,x})$  i.

$f_t(y) = \sigma(W_{f,y}[h_{t-1}^y, y_t] + b_{f,y})$  ii.

Input Gates:

$i_t(x) = \sigma(W_{i,x}[h_{t-1}^x, x_t] + b_{i,x})$  ii.

$i_t(y) = \sigma(W_{i,y}[h_{t-1}^y, y_t] + b_{i,y})$  iii.

Tan h Layer:

$\tilde{C}_t = \tan h(W_{Cx}[h_{t-1}^x, x_t] + b_{cx}) + \tan h(W_{Cy}[h_{t-1}^y, y_t] + b_{cy})$  ii.

Update:

$C_t = \text{mean}(f_t(x), f_t(y)) * C_{t-1} + \tilde{C}_t$

Output Gates:

$o_t(x) = \sigma(W_{o,x}[h_{t-1}^x, x_t] + b_{o,x})$  ii.

$o_t(y) = \sigma(W_{o,y}[h_{t-1}^y, y_t] + b_{o,y})$  iii.

The Tan h layer merges the two paths into a shared cell state.

Figure 21:
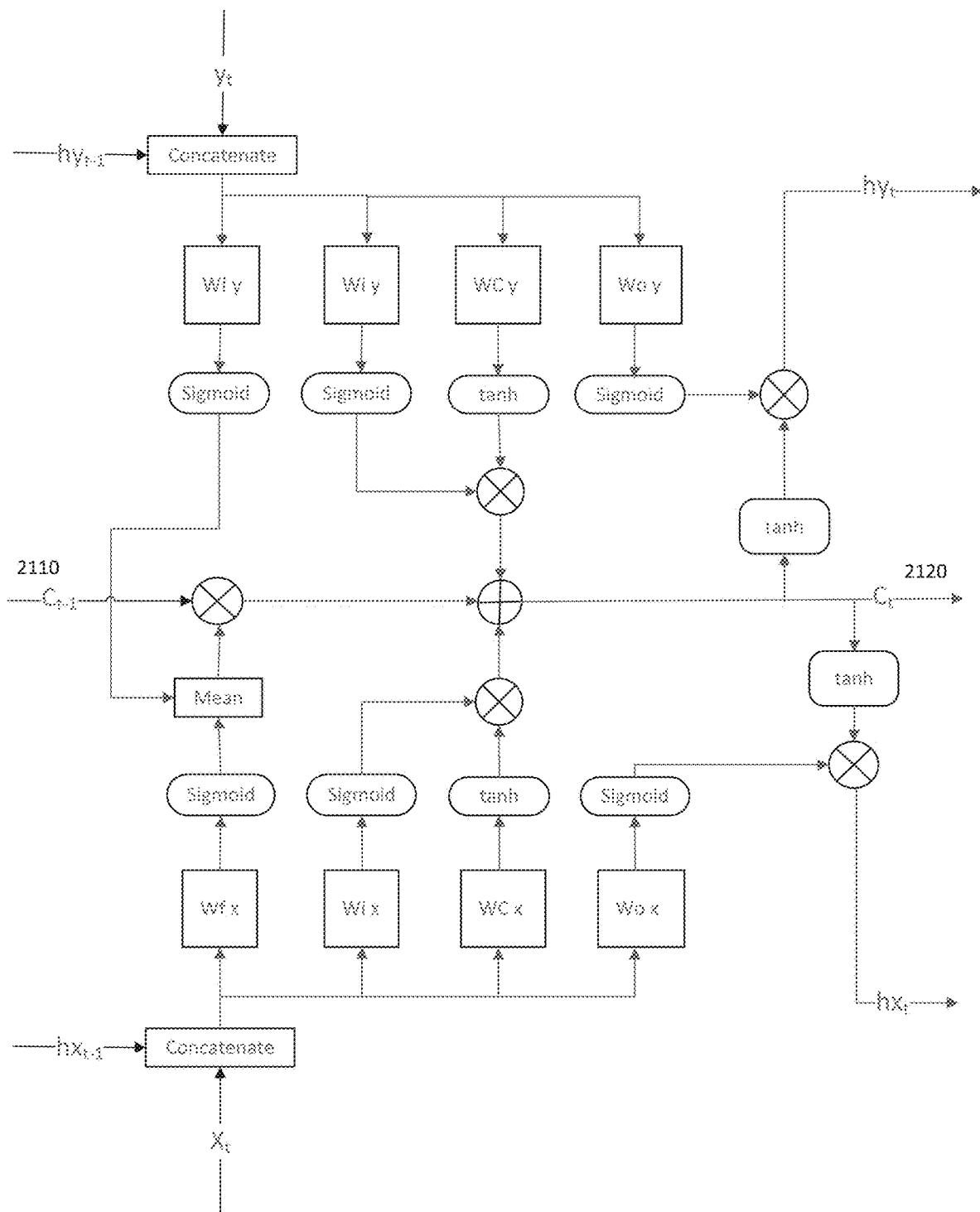
FIG. 21 is a block diagram of an embodiment for a portion of an example multi-modal (MM) long short-term memory (LSTM) showing the fusion of LSTM states as input, and signals as separate input.

FIG. 21 is a block diagram of an embodiment for a portion of an example multi-modal (MM) long short-term memory (LSTM) showing the fusion of LSTM states as input, and signals as separate input. The MM-LSTM can facilitate multiple different inputs. Through a forward pass of the developed MM-LSTM, two inputs x and y are kept independent for most of the path. A separate hidden state is maintained for each of the separate inputs. These are maintained separately by routing through unique sets of neural network weight matrices.

To determine the amount of information to forget from the cell state 2110, the forgetting coefficients are first computed for each input. These are each in the range of zero to one. They are then routed together through a mean block, which computes the average scaling coefficient with which to multiply the cell state 2110. This result is multiplied by the cell state element-wise to scale each entry by the same factor between zero and one. For updating the cell state 2110 through addition, the combined output of a tan h layer from each separate path are added to the cell state. The result is a new cell state 2120, to be used for the next time step. This cell state is routed through a tan h block, and this output is multiplied with each output gates to yield the new updated, separate hidden states. As another embodiment, the system may use the state of single LSTMs that are operating on a single feature. Some of the inputs to a MM-LSTM can be the hidden state from other LSTMs, such as from LSTMs 520, 522, 524 shown in FIG. 5.

Figure 6:
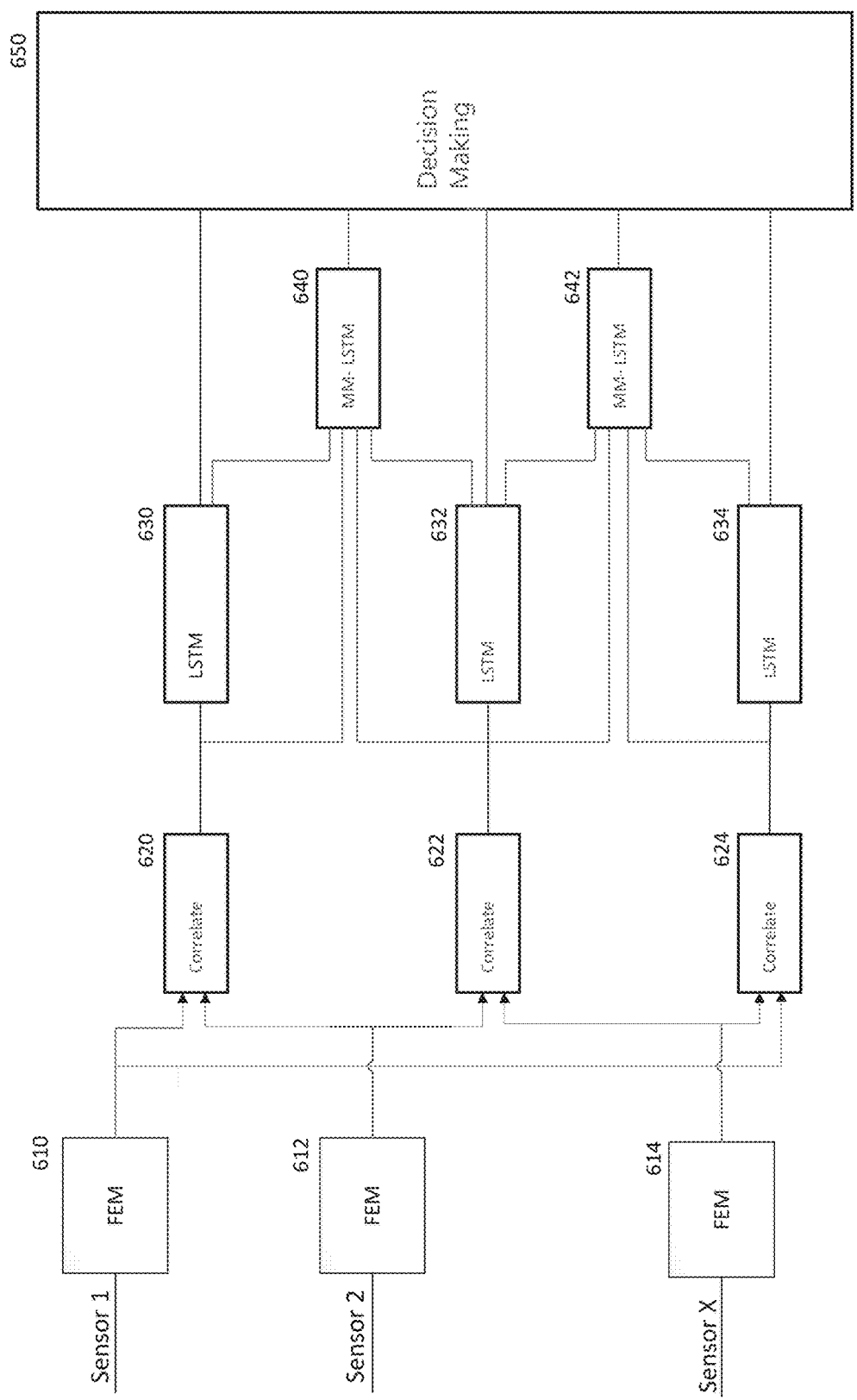
FIG. 6 is a block diagram of another embodiment for processing human physiological signals through decision making such as performed on the system of FIG. 1.
Figure 7:
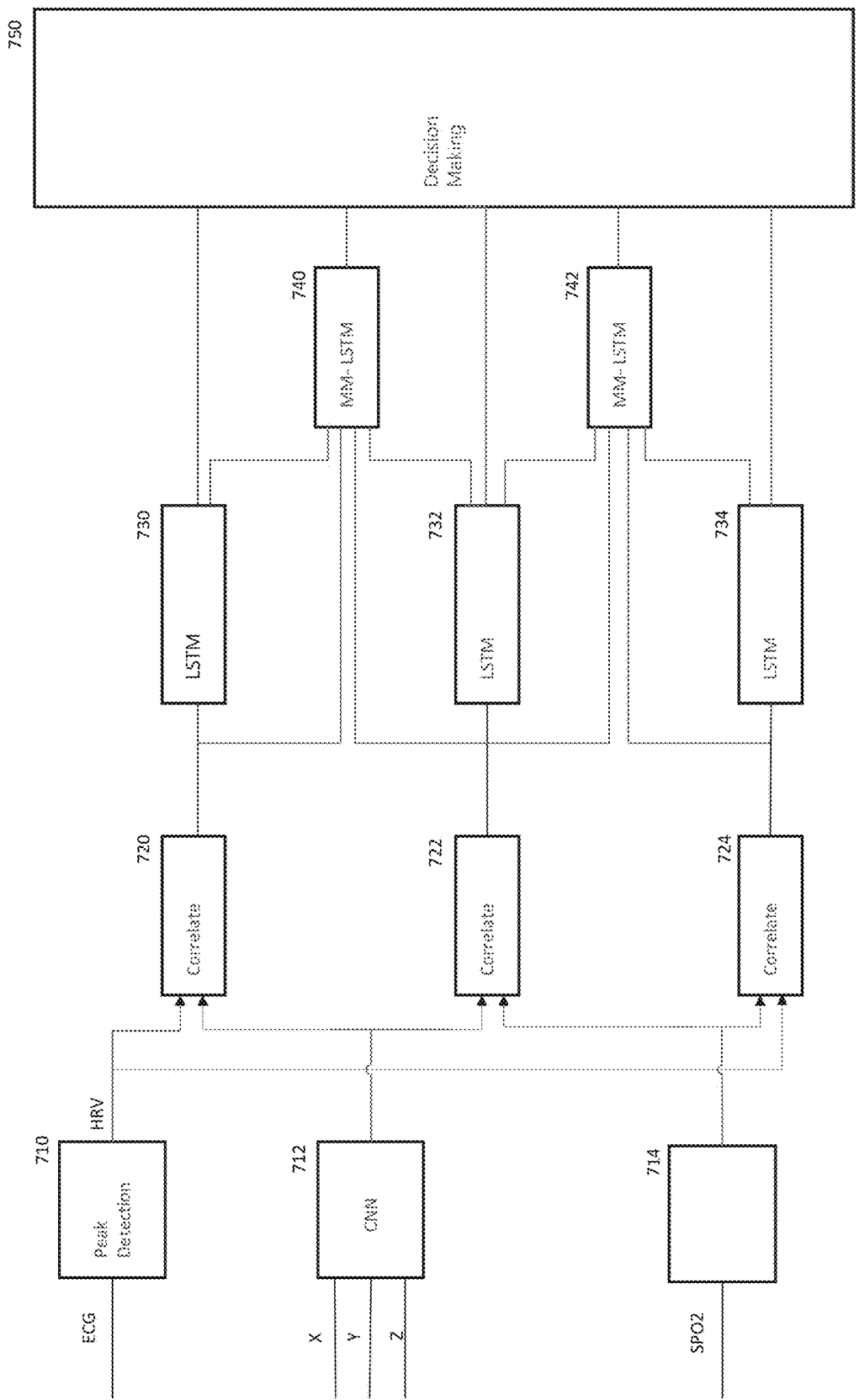
FIG. 7 is a block diagram of another embodiment for processing human physiological signals through decision making such as performed on the system of FIG. 1.
Figure 22:
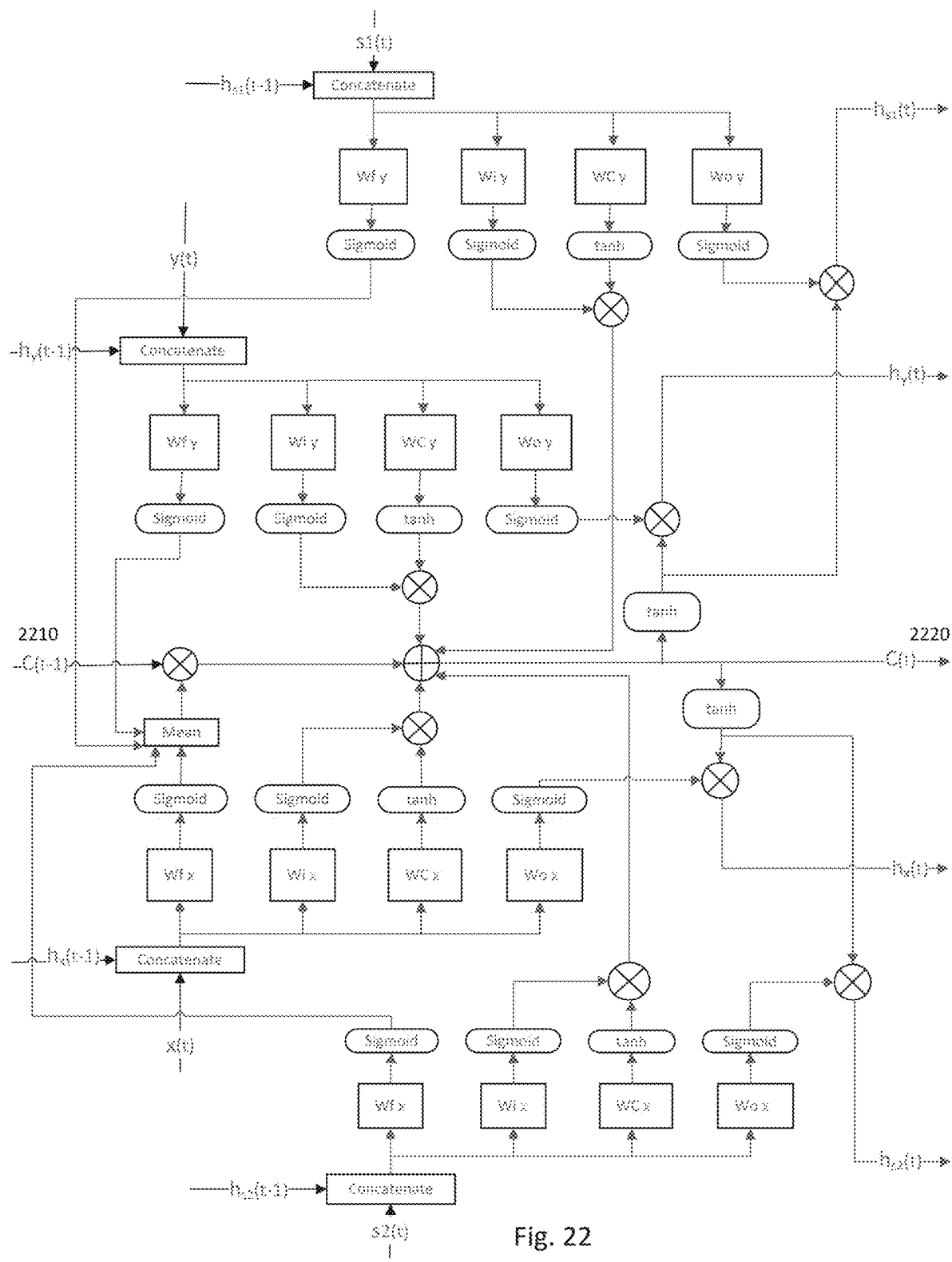
FIG. 22 is a block diagram of an embodiment for a portion of an example MM-LSTM showing how both signals and hidden states from other LSTMs can be combined inside of the MM-LSTM.

FIG. 22 is a block diagram of an embodiment for a portion of an example MM-LSTM showing how both signals and hidden states from other LSTMs can be combined inside of the MM-LSTM. FIG. 22 shows a cell state 2210 and a new cell state 2220 and also shows how both signals and hidden states from other LSTMs can be combined inside of the MM-LSTM, such as in MM-LSTM 530, 532 described with respect to FIG. 5. This embodiment can provide a significant innovation over "vanilla" LSTMs by combining multiple raw signals from different modalities with the changing states of other LSTMs entrained on the dynamics of those signals. Additional inputs in FIG. 22 are routed through the same mean and summation blocks as in FIG. 21. The output from output gates is multiplied with the same tan h(Ct) as in FIG. 21. These networks are used in components 530, 532 shown in FIG. 5, 640, 642 shown in FIG. 6, 740, 742 shown in FIG. 7, 830, 832 shown in FIG. 8, and 960, 962, 964 shown in FIG. 9. This distributed training may happen on the edge system 130, 150 and the cloud 110 for supervised learning shown in FIG. 1.

For a machine learning model with many input features, or a large multi-dimensional input, it is often useful to prune the number of features that are fed into the model. This can save processing time and storage.

One method of feature selection can be described as recursive feature elimination (RFE). For a dataset with N features, RFE tries to find a subset of k<N features that yield a validation accuracy within some threshold of the accuracy obtained by using the full feature set.

For each model of size m, where k<m<=N, the features are ranked according to their importance, or their contribution to model accuracy. The least important feature is removed, and the model is trained again on m−1 features. This process is repeated until only k features remain, or until validation accuracy falls below threshold.

In some embodiments, for a given task or objective by using an appropriate feature selection scheme, the features that gain highest correlation with labels on associated data samples are selected. After the feature selection for a given task or objective, the cloud 110 may change model configuration in the edge system 130, 150 based on a given objective. These on-the-fly reconfigurable models allow our technology to offer multiple objectives and services for health care, including but not limited to acute heart failure prediction, myocardial infarction prediction, arrhythmia detection, orthostatic hypertension detection, etc.

FIG. 6 illustrates another embodiment of a novel machine learning approach where the system 100 incorporates a scheme to learn over an extended period in time. In this embodiment a correlation sub-system 620, 622, 624 is utilized along with multi-level modified LSTMs 630, 632, 634, 640, 642, which work together to summarize longer sequences into a decision.

A feature extraction sub-system 610, 612, 614 computes features from sensory signals received from Sensor 1 to Sensor X. For example, heart rate variation can be computed from an electrocardiogram (ECG) signal sensed from the heart, and sitting or walking and a number of steps can be computed from X, Y, Z acceleration signals as a feature representing physical activity.

The correlation sub-system 620, 622, 624 computes correlation of two features derived from one or more sensory signals. Each pair of signals may be routed to one of the correlation blocks 620, 622, 624, whose correlation signal outputs are sent to an LSTM 630, 632, 634.

For example, congestion of the lungs can be extracted from signals recorded by a thoracic bioimpedance sensor. Correlation sub-systems 620, 622, 624 may estimate correlation between two signals, such as drops in HRV and lower activity; more congestion and higher percentage of AFIB; more congestion and lower activity; lower oxygen saturation level with lower physical activity. These high correlations may be bio-markers that help to predict increasing risk of acute heart failure.

FIG. 6 takes the Multi-Level Modified deep learning approach where each correlation output of pair of candidate features go through a first LSTM group 630, 632, 634 to learn a pattern on one of bio-markers and then go through an MM-LSTM 640, 642 to learn patterns on combinations of two or more of bio-markers plus inputs from a state of the first group of LSTMs 630, 632, 634. The output of first groups of LSTMs and the second group of LSTMs may be combined in a late fusion block that may perform decision making 650. This block is identical to decision making 540 shown in FIG. 5. The different kinds of decisions are described in conjunction with FIG. 17. This distributed training happens on the edge and the cloud for supervised learning.

FIG. 7 is a block diagram of another embodiment for processing human physiological signals through decision making such as performed on the system of FIG. 1. The block diagram depicted in FIG. 7 is functionally similar to the one illustrated in FIG. 6 with the exception of specific examples of signal-processing blocks for each feature extraction module 610, 612, 614. The remaining portions of FIG. 7 are functionally similar to that of FIG. 6.

In some embodiments, a peak detection block 710 uses an algorithm that finds the R peak from the QRS component of an ECG signal, and returns a peak-to-peak interval referred to as a R-R interval. HRV can be computed from statistical properties of R-R intervals. Physical activity represents an important metric of daily health. A block 712 can take as its input a signal from an accelerometer sensor and summarize the data into various measurements of physical activity, such as step count (the number of steps taken by the patient) or calories burned, within some time interval. These measurements of physical activity can be computed onboard the sensor, or computed by the block 712 using a convolutional neural network (CNN) or other machine learning model (such as random forest, etc.) to process the raw 3-axis signal from the accelerometer.

One particular scheme to process the raw accelerometer X, Y, Z data is to first use a random forest to classify the type of activity from these values. These types of activity include sitting, lying down, walking, etc. When walking is detected, the number of steps are found by counting the number of peaks within the smoothed signal. Steps are usually most prominent along the Z axis, depending on sensor orientation. $SpO_2$ is measured from light sensors on the skin. A feature block 714 can take as its input the detected $SpO_2$ signal from a wearable sensor and relay the signal forward to the correlation sub-system. Correlation blocks 720-724, LSTMs 730-734, MM-LSTMs 740 and 742, and a decision making block 750 are similar to those of FIG. 6.

Figure 8:
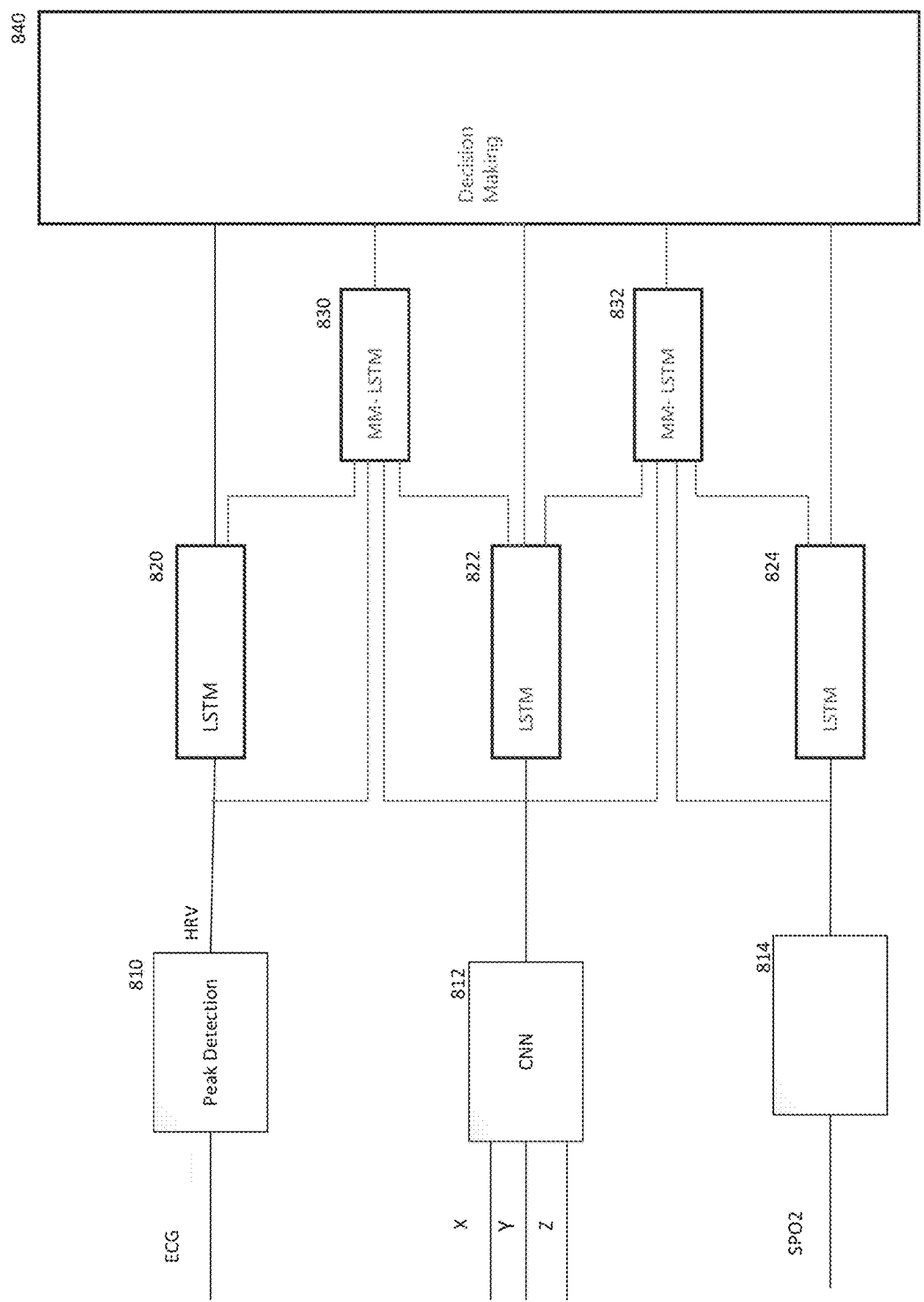
FIG. 8 is a block diagram of another embodiment for processing human physiological signals through decision making such as performed on the system of FIG. 1.

FIG. 8 is a block diagram of another embodiment for processing human physiological signals through decision making such as performed on the system of FIG. 1. The block diagram depicted in FIG. 8 is similar to the one illustrated in FIG. 7. Features detected at blocks 810, 812 and 814 are passed directly into respective LSTMs 820, 822 and 824. This makes it functionally similar to that illustrated in FIG. 5 with the exception of specific examples of signal-processing blocks for each feature extraction module 510, 512, 514. MM-LSTMs 830 and 832, and a decision making block 840 are similar to those of FIG. 7.

In the configuration of FIG. 8, pairs of features are sent together into an MM-LSTM 830, 832. In one embodiment of a MM-LSTM, one separate path is used for each modality of incoming time series data. These separate signal types are merged in the model at the time the cell state of the LSTM is updated. The gate functions are modified to be able to input more than one time series or features extracted from more than one time series to a single LSTM to combine learning from patterns on both signals. Any significant changes in two signals that are related or correlated to each other but may have a lag respect to each other are identified.

FIG. 9 is a block diagram of another embodiment for processing human physiological signals through decision making such as performed on the system of FIG. 1. Figures shows one implementation of feature extraction and machine learning algorithms. In the arrangement illustrated in FIG. 9, pairs of features are passed into various blocks, whose outputs are integrated by a decision maker 970. The types of features may include, but are not limited to, an arrhythmia percentage 910, a heart rate variability (HRV) 912, physical activity 914, and blood oxygen saturation $SpO_2$ 916.

An arrhythmia detector 910 performs detection of cardiac arrhythmias. The arrhythmia detector 910 may include a CNN, whose output is analyzed by an LSTM, and an attention layer which processes the LSTM output. First, the CNN searches for certain features, like heart-beat frequency and shape, across the length of the ECG signal. The CNN can also provide temporal downsampling to the signal via pooling layers. The output of the CNN represents compressed temporal features over time. These are fed to an LSTM which is well-suited for time-series analyses. Finally, the returned sequences from the LSTM are fed through an attention layer, which performs multi-class classification through a Softmax layer.

The attention layer helps the model to be more interpretable, by providing a visual indication to the medical provider that highlights the relative contribution of each segment of the input signal to the classification decision made by the model.

Another way to increase interpretability of machine learning models is by using a technique called class activation mapping (CAM). A class activation map for a particular category or class indicates the discriminative regions of the input signal used by the model to identify that category. In the case of an ECG signal, for instance, this would show which portions of the ECG trace were most influential in leading to the prediction of a certain arrhythmia class.

Figure 10:
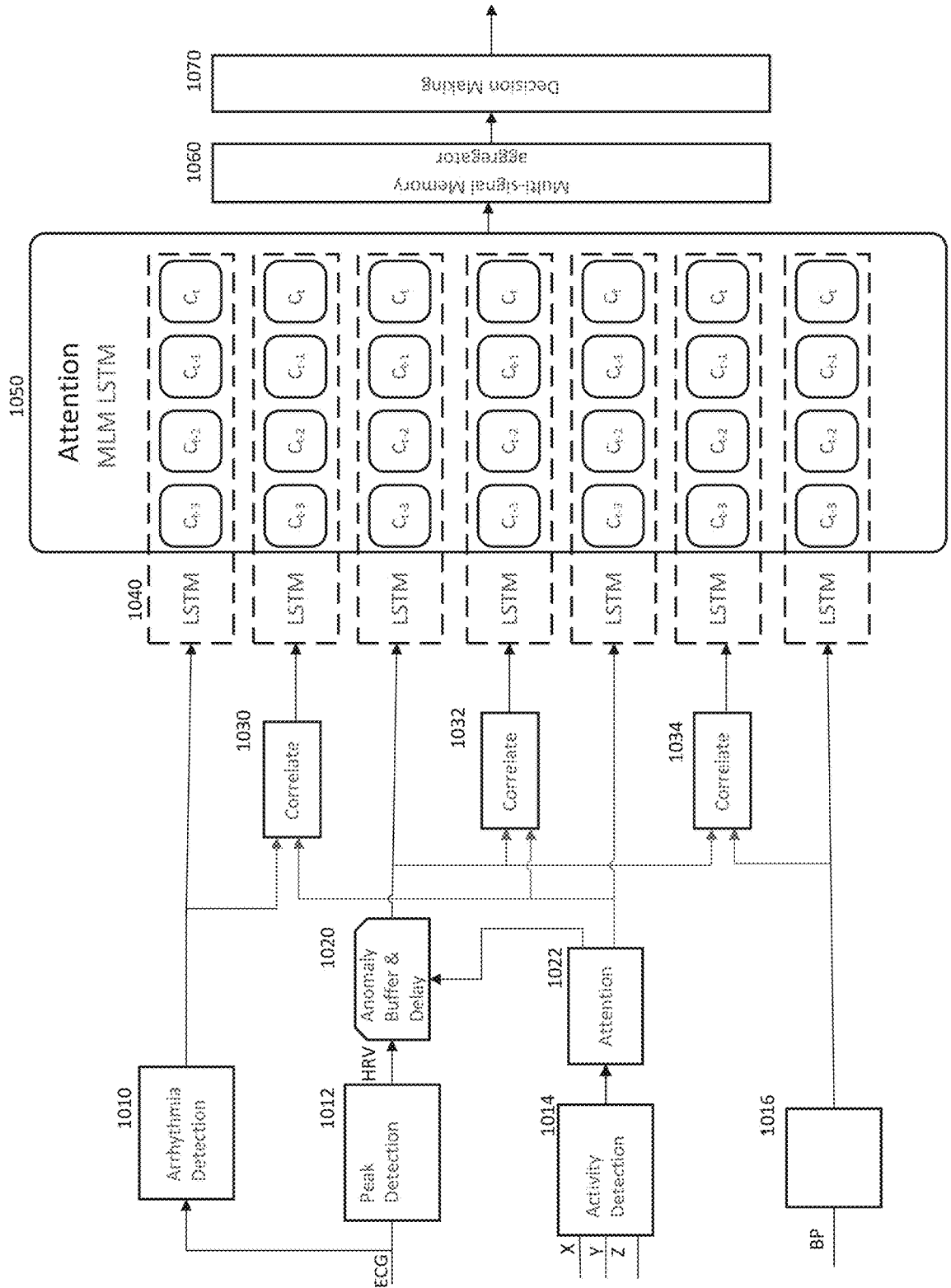
FIG. 10 is a block diagram of an embodiment for processing human physiological signals through decision making and including an example attention network and an example multi-signal memory aggregator such as performed on the system of FIG. 1.

For each segment of an incoming ECG signal, the arrhythmia detector 910 can output a number that represents the proportion of that segment containing arrhythmia. For example, for a 10-beat segment with a single premature ventricular contraction, the percentage of PVC would be 10%. A sequence of these arrhythmia proportions can be combined with another signal using a correlation block, such as illustrated in FIGS. 9 and 10, or combined with another signal directly into an MM-LSTM as illustrated in FIG. 9. Alternatively, these proportions are used alone as time-varying input into one of a bank of LSTMs as illustrated in FIG. 10.

A peak detection block 912 is identical in input, processing, and output to earlier instances of the peak detection blocks 710 of FIGS. 7 and 810 in FIG. 8. A physical activity block 914 is identical in input, processing, and output to earlier instances 712 of FIGS. 7 and 812 in FIG. 8. A $SpO_2$ block 916 is identical in input, processing, and output to earlier instances 714 of FIGS. 7 and 814 in FIG. 8.

Each pair of the signals from the feature blocks 910, 912, 914, 916 is routed to a correlation block 940, 942, 944, whose correlation signal output is sent to an LSTM 950, 952, 954. These pairs are also sent together into an MM-LSTM 960, 962, 964. In one embodiment of MM-LSTM, one separate path is used for each modality of incoming time series data. These separate signal types are merged in the model at the time the cell state of the LSTM is updated. The gate functions of the LSTM are modified to be able to input more than one time series or features extracted from more than one time series to a single LSTM to combine learning from patterns on both signals. Any significant changes in two signals that are related or correlated to each other but that may have a lag respect to each other are identified. This functionality is illustrated and described in conjunction with FIG. 9, FIG. 21 and FIG. 22. Both the LSTM and MM-LSTM outputs are sent to the decision maker 970 that is further described in conjunction with FIG. 17.

Another embodiment we have labeled as a multi-level modified LSTM or MLM RNN. In this embodiment, a separate LSTM is used for each modality, and the modalities are used in the following manner. An Attention layer attends over consecutive cross-modality cell states. This Attention layer has an elastic mechanism to aggregate different data-rate inputs and capture correlation between different time intervals of inputs having a wide attention strip (2-D attention heat map). The output is fed into a gated memory to store a history of cross-modality interactions. This is described in more detail in conjunction with FIG. 10 (also in FIG. 3 for the MLM RNN).

In the embodiment of FIG. 9, the HRV of the peak detection block 912 and the step count of the activity block 914 may need to be buffered in an anomaly buffer & delay block 920 and aligned before passing into the correlation blocks. For activity detection, an attention block 922 is used to identify regions of low activity. This block 922 may be used to find important segment(s) of an input signal, along with a classification decision to categorize the input signal. The new output is used to locate certain patterns in the input signal in order to highlight the corresponding time-steps for downstream blocks. In an example, step counts or activity type are used as an input, and produce a heat map of detecting decrease in activity as a new output of the attention block 922 to feed to MM LSTM 960 and correlation block 942. A buffered HRV signal, along with the attention map, are passed into a correlation block 942. Additional destinations for the attention map are correlation block 940, which computes the cross-correlation with arrhythmia percentage; and the MM-LSTM 962 which combines it with the buffered HRV 920.

As incoming signals are recorded, they are saved in a rolling buffer such as an anomaly buffer & delay block. This enables the system to always keep a recent signal history ready for computation. The rolling buffer starts out empty, and begins filling with incoming data by concatenating new samples onto the end. When the buffer reaches a predetermined length, the oldest values inside of the buffer are removed, and the remaining values are shifted to allow room for the new values to append onto the end of the most recent values.

In some embodiments, the system 100 can detect when patient vital signs deteriorate (anomaly detection). One way that this is achieved is by using threshold detectors or a modified attention network described below or by arrhythmia detection. These anomaly detection blocks 920, 922 function as a switch that starts a sequence of events when the input signal is determined to cross a certain threshold. Example thresholds may include, but are not limited to: resting heart rate above about 100 bpm, $SpO_2$ falling below about 85% or a drop of more than about 10 points in a short time, and HRV decrease before activity decrease.

There are many bio-signals whose values can be used to directly decode patient status. Examples include heart rate variability and physical activity. In some cases, a state change indicated by one changing signal commonly precedes another state change in a separate bio-signal by some interval. An example is a decrease in HRV hours before a decrease in physical activity. For these two signals, their cross-correlation represents an important feature describing their temporal interactions. The modified attention block as designed by the developer helps to first, detect lower physical activity state and second, run cross correlation in the most efficient way to save processing power and power consumption on the edge system 130, 150. This allows the edge to be a smaller size and portable for outdoor use (so as connect to a cellular IOT network) and lower cost.

Two options may be used for the correlation blocks as follows:

Option 1: For a given pair of signals, if a threshold-crossing is triggered for one of the signals, that signal is routed along with a separate signal into a correlation block. Then, cross-correlations are computed for the pair of signal buffers.

Option 2: For a given pair of signals, if a threshold-crossing is triggered for one of the signals, it registers active as an event and will wait for another signal threshold-crossing-detector. When both signals have crossed their corresponding thresholds, the correlation block becomes active. Then, cross-correlations are computed for the pair of signal buffers.

A lag can be computed in some cases based on simple threshold crossing blocks applied on both inputs to a correlation block. The correlation block takes as input the two input signals and the time-lag to output a new representation of the two signals, aligned at the time of the second signal threshold crossing. After aligning these two inputs, they are input not only to the correlation block 942 but also to the multi-modal LSTM block 962 that may learn some cross-signal interactions.

The time-varying correlation signal can be fed as input to an LSTM 952 that is interested in the time-course of the correlation output itself. For example, sharp (smooth) peaks in the correlation signal represent a more transient (long-lasting) correlation in time. This signal can be used alone by an LSTM 920, 930.

As shown in FIG. 9, the ECG signal goes through the peak detection block 912 to detect the R peak in QRS portion and consequently compute the RR interval which is used to derive HR and HR variation (HRV). Some embodiments use a bi-directional LSTM to detect R peaks; however training of this LSTM can happen as a subtask before training of the main model for the main task or objective such as acute heart failure prediction based on the multi-modal LSTM 960, 962, 964, 970 of FIG. 9 or the multi-level LSTM 1040, 1050, 1060 to be described in FIG. 10.

Some signals may contain important features which cannot be detected by simple threshold crossings. This presents a challenge for properly aligning two input signals to an LSTM for the purpose of finding interactions. In the solution utilized by the system 100, the attention block 922 is utilized for finding regions of interest of its input signal.

For some time-varying features, like physical activity, some embodiments exploit the capabilities of the attention layer to both categorize the input signal into one of multiple classes, and to return a time-varying signal that represents a heat map over time on the input. This heatmap can be used as an input to correlation block as in the correlation block 940, or as an input to an LSTM 962 combined with other physiological signals. This represents a novel way of using attention weights, representing a heatmap, in a manner that combines the extracted characteristics of one signal with other raw signals.

Each type of vital sign represents a unique view into the patient's current health status. These vital signs each have their own individual representation space and dynamics. From a collection of vital signs of separate modalities (e.g. heart rate, heart rate variation, BP, $SpO_2$, physical activity), some of the signals may share some mutual information due to dynamics of interactions between different organs such as the heart, lung and nervous system, while containing some separate independent information about the patient's current status. To achieve a more complete view of the time course of patient condition, multiple modalities are combined in some modules, such as the correlation block 940, 942, 944 and MM-LSTM 960, 962, 964.

Finally, all engineered outputs and predictions are combined and interpreted by the decision maker 970. The different kinds of decisions are described in conjunction with FIG. 17.

FIG. 10 is a block diagram of an embodiment for processing human physiological signals through decision making and including an example attention network and an example multi-signal memory aggregator such as performed on the system of FIG. 1. Referring to FIG. 10, memory fusion layers are described. Due to the different time course of separate bio-signals, and the different kinds of temporal features they may contain, it can be confusing for a single LSTM to make sense of input data including several distinct signals. To achieve a union of signal analysis across different types, some embodiments extend a memory fusion network to operate on a combination of bio-signals in the architecture shown in FIG. 10.

In certain embodiments, the arrhythmia detection block 1010 is identical to the arrhythmia detection block 910 described with respect to FIG. 9. The peak detection block 1012 is identical to the peak detection block 912 described with respect to FIG. 9. The activity detection block 1014 is identical to the activity detection block 914 described with respect to FIG. 9. In this embodiment, blood pressure 1016 is used instead of $SpO_2$ 916. The anomaly buffer & delay 1020 is identical to the anomaly buffer & delay 920 described with respect to FIG. 9. The attention block 1022 is identical to the attention block 922 described with respect to FIG. 9. The correlation block 1030 is identical to the correlation block 940, and the correlation block 1032 is identical to the correlation block 942, described with respect to FIG. 9. The correlation block 1034 only differs from the correlation block 944 of FIG. 9 by using blood pressure instead of $SpO_2$. The system 100 takes as its input one or more measurable bio-signals from wearable or implanted sensors. These bio-signals may include, but are not limited to: ECG, activity, blood pressure, $SpO_2$, respiration, bio-impedance, and body weight.

First, each signal type is routed alone to its own LSTM 1040 within a bank of LSTMs. Pairs of signals are also routed into correlation blocks 1030, 1032, 1034, whose outputs are each sent to one of the LSTMs 1040. The group of LSTMs 1040 processing separate signals is considered collectively as a bank. A history of states from each of these LSTMs 1040 is collected, and analyzed by an attention network 1050. The output of this attention network learns interactions across time and across signals. A history of these interactions is summarized using a Multi-signal memory aggregator 1060.

In this embodiment, the bank of LSTMs and the attention network 1050 work together as an encoder, selecting the relevant information to pass to the next layer. The Multi-signal memory aggregator 1060, then, works as a decoder to help generate a prediction from the states output by the encoder. A decision maker 1070 makes the final decision by transforming the output of the multi-signal memory aggregator 1060, similar to the decision maker 540 described with respect to FIG. 5, but without needing to concatenate multiple vectors into one.

Figure 11:
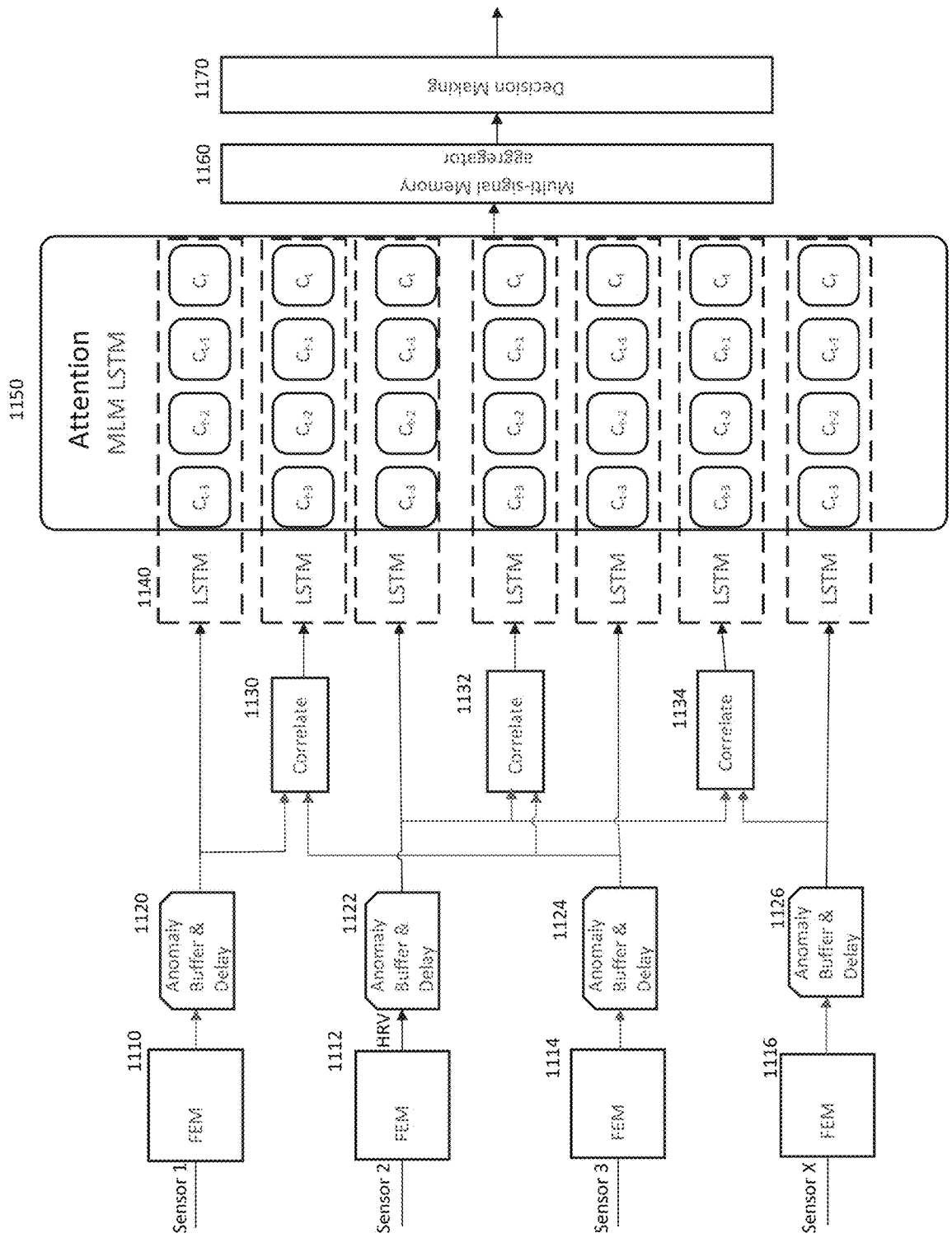
FIG. 11 is a block diagram of another embodiment for processing human physiological signals through decision making and including the attention network and the multi-signal memory aggregator such as performed on the system of FIG. 1.

FIG. 11 is a block diagram of another embodiment for processing human physiological signals through decision making and including the attention network and the multi-signal memory aggregator such as performed on the system of FIG. 1. The sub-system depicted in FIG. 11 is identical to that illustrated in FIG. 10, except that generic signals are routed through unspecified feature extraction modules. This configuration shows how an arbitrary combination of features extracted from a collection of sensors 1110, 1112, 1114, 1116 can be routed through anomaly detection blocks 1120, 1122, 1124, 1126 and then sent through LSTMs 1140 and MLM-LSTMs 1150 before or after combining with another feature through cross-correlation via correlation blocks 1130, 1132, 1134. Unprocessed or cross-correlated features are passed through a bank of LSTMs 1140. The remaining signal paths through components 1150, 1160, 1170 are functionally identical to those depicted in components 1050, 1060, 1070 in FIG. 10.

Figure 12:
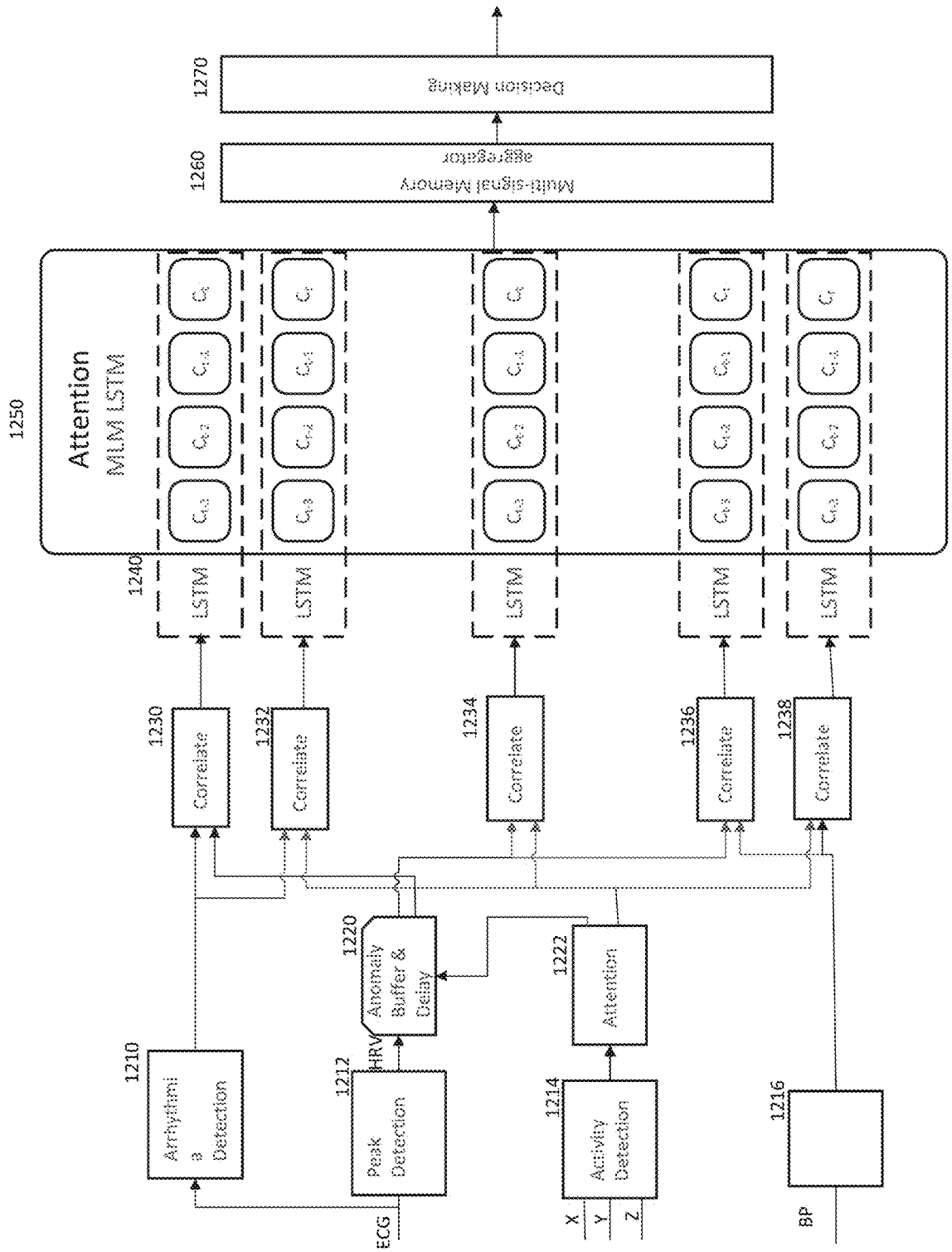
FIG. 12 is a block diagram of another embodiment for processing human physiological signals through decision making and including the attention network and the multi-signal memory aggregator such as performed on the system of FIG. 1.

FIG. 12 is a block diagram of another embodiment for processing human physiological signals through decision making and including the attention network and the multi-signal memory aggregator such as performed on the system of FIG. 1. The sub-system depicted in FIG. 12 is similar that illustrated in FIG. 10, but the input to each LSTM 1240 in MLM_LSTM includes only the outputs from correlation blocks 1230, 1232, 1234, 1236, 1238. The remaining blocks 1210, 1212, 1214, 1216, 1220, 1222, 1250, 1260 and 1270 are similar to those of FIG. 11.

Figure 13:
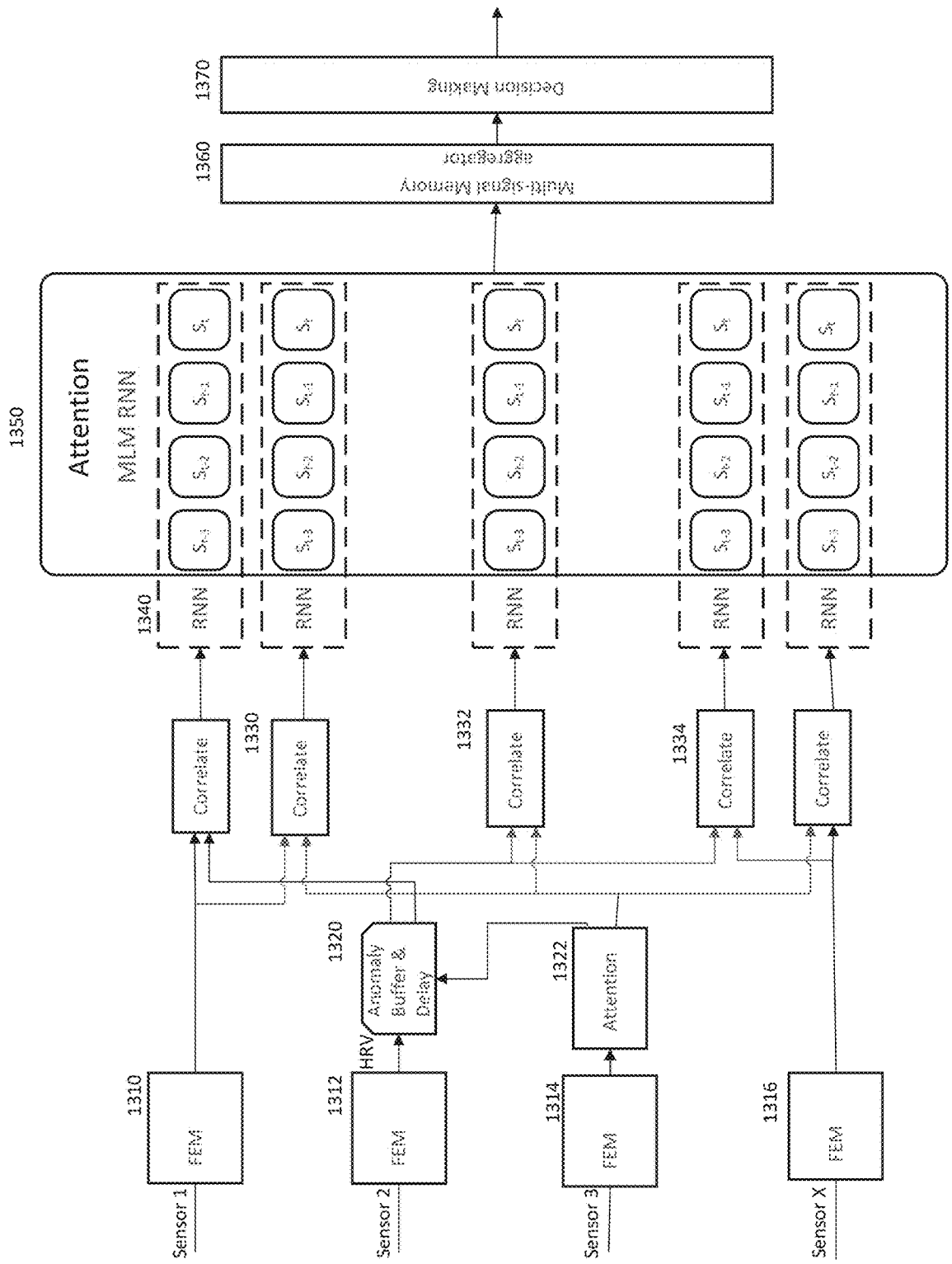
FIG. 13 is a block diagram of another embodiment for processing human physiological signals through decision making and including the attention network and the multi-signal memory aggregator such as performed on the system of FIG. 1.

FIG. 13 is a block diagram of another embodiment for processing human physiological signals through decision making and including the attention network and the multi-signal memory aggregator such as performed on the system of FIG. 1. The sub-system depicted in FIG. 13 is the same as that illustrated in FIG. 12, but here the LSTM blocks 1240 are replaced with RNNs 1340. This is used to illustrate how the bank of LSTMs can be replaced by a bank of any recurrent neural architecture. The remaining blocks 1310, 1312, 1314, 1316, 1320, 1322, 1330, 1332, 1334, 1350, 1360 and 1370 are similar to those of FIG. 12.

Figure 14:
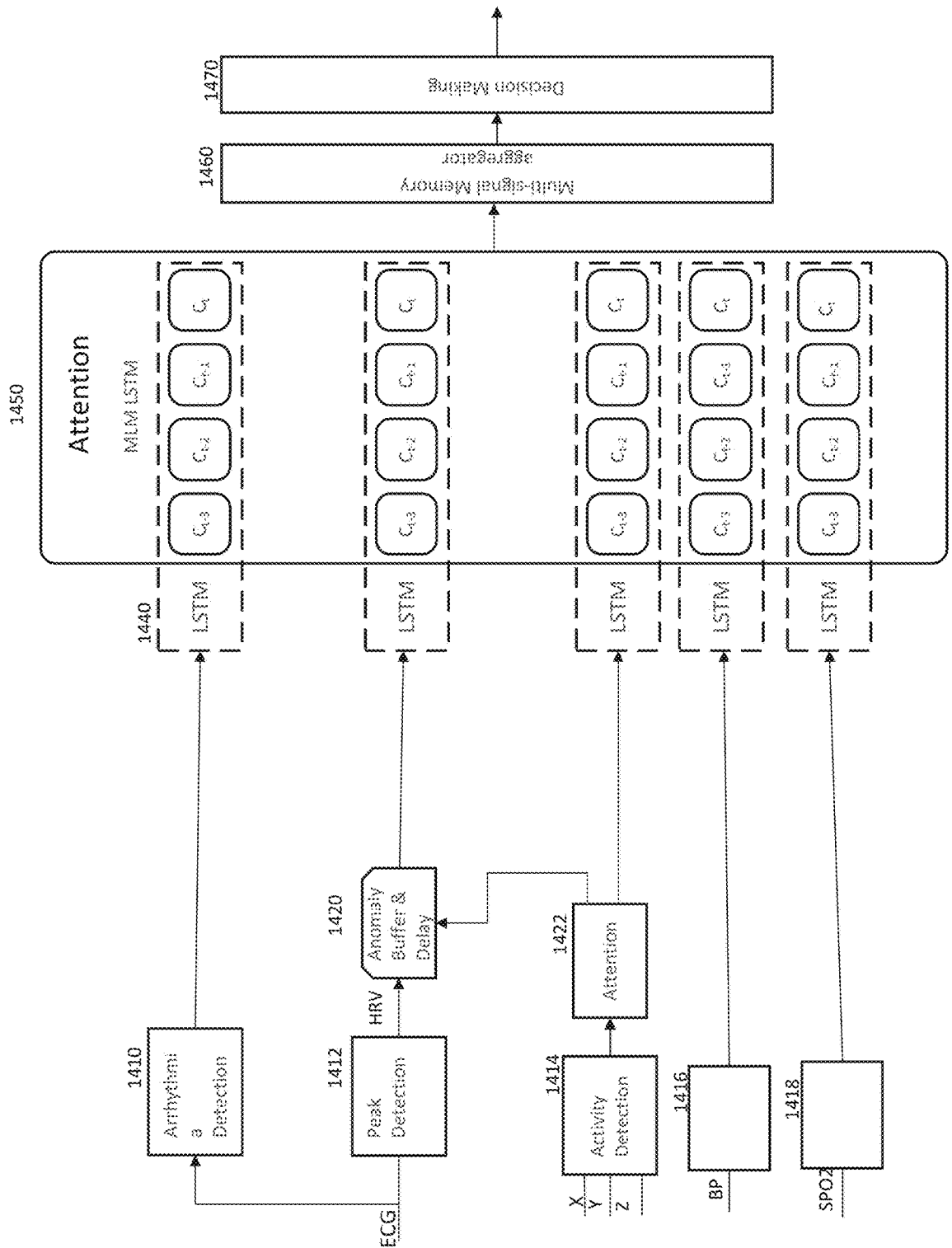
FIG. 14 is a block diagram of another embodiment for processing human physiological signals through decision making and including the attention network and the multi-signal memory aggregator such as performed on the system of FIG. 1.

FIG. 14 is a block diagram of another embodiment for processing human physiological signals through decision making and including the attention network and the multi-signal memory aggregator such as performed on the system of FIG. 1. The sub-system depicted in FIG. 14 is identical to previous examples of MLM_LSTM except that it eliminates the correlation blocks altogether and includes an SPO2 block 1418. The remaining blocks 1410, 1412, 1414, 1416, 1420, 1422, 1440, 1450, 1460 and 1470 are similar to those of FIG. 13.

Memory Fusion: More Details

Each of the different input signals is first passed separately into one of the LSTMs 1040 within a bank of LSTMs. Each LSTM in this bank can learn temporal features for a specific signal type. Utilizing a bank of separate LSTMs allows each type of signal to have a different input, memory (cell state), and output shape, which provides flexibility for combinations of signals with different sample rates.

FIG. 15 is a block diagram of the example attention network and multi-signal memory aggregation in more detail. FIG. 15 shows the modified attention network and the multi-signal memory aggregation in more detail. The cell states from the bank 1540 of LSTMs are buffered and passed into the attention network 1550, which finds interactions across the different signals and across time; these interactions are reflected in each of the two dimensions of its output. To compute the attention output X, the input sequence of signal states is transformed into a matrix of scaling factors of the same shape as the input, by a fully connected neural network (FCNN) 1510 with Softmax activation 1520. This matrix represents the attention coefficients across signals and across time, effectively capturing interactions across both domains. This matrix is combined with the input states through element-wise multiplication to produce the attention map 1557, the cross-signal information used as input for the multi-signal memory aggregator 1560. The multi-signal memory aggregator 1560 can include sub-blocks such as attention map for timestep 1562, 1564 and 1566.

The modified attention layer over consecutive cross-modality cell states can be defined as:

$$X_{s,t} = B_t \odot \frac{\exp(a_{s,t})}{\sum_{s',\tau} \exp(a_{s',\tau})}$$

where
X=attention map $B_t$=cross-modality cell-state buffer
$a_{s,t}=W_a*B_t$ ($W_a$=FCNN 1510)

This modified attention layer can search over its input of time-locked mini-sequences from different signals and identify important patterns within subsets of these signal types. For example, as described with respect to FIG. 10, during the attended window 1050, systolic BP 1016 could be decreasing while arrhythmia percentage 1010 is increasing. The attention layer 1550 can learn that this combination is especially risky, and weight the appropriate elements of its output accordingly.

The strategy of attention over states can be applied to any collection of elements within a bank of recurrent neural networks. These elements could be from any type of recurrent neural architecture, including vanilla RNNs, LSTMs, or others. In the case of vanilla RNNs, these elements are hidden states, while in the case of LSTMs, these elements could be hidden states or cell states. In either case, attention can be applied to a buffer of states. FIG. 18 illustrates a way that attention can be applied to various recurrent neural architectures.

Referring back to FIG. 15, the cross-signal information from attention is stored over time in the multi-signal memory aggregator 1560, a modified LSTM that updates its own state as a function of the attention output and its own stored memories. This model can capture a longer history of interactions across signal types and across time. The output of the multi-signal memory aggregator 1560 is fed into a decision making block 1570 for prediction.

FIG. 16 is a block diagram of an example attention map at a particular time step and multi-signal memory aggregation in more detail. FIG. 16 shows example components 1600 of the multi-signal memory aggregator 1560 of FIG. 15. The multi-signal memory aggregator may include three gates. An input gate simply passes the input 1610 of the attention map for a time step through a neural network layer with linear activation to construct a proposed update to the internal cell state. An update gate involves a separate neural network with sigmoid activation whose output dictates how much of the information in the proposed update to incorporate into the cell state at the next time step. The update and input gates are depicted in a dashed block 1620. A retention gate depicted by a dashed block 1630 involves another neural network with sigmoid activation whose output is used to control the amount of information to maintain from the previous cell state itself. Each of these gates can take as their input the output from the attention block 1610. The output from each of these gates is summed in a dashed summation block 1640. This sum Ct is passed to a decision making neural network 1670 and is also stored in a memory 1650 for a next time step.

The multi-signal memory aggregator 1560 can store a history of cross-modality interactions based on the following definitions:

1. Update Gate:
   b. $u_t=W_i(X) \odot \sigma(W_u(X))$
   c. X: input from attention
   d. $W_i$: Fully-connected neural network (FCNN)
   e. $W_u$: FCNN
2. Retention Gate:
   a. $r_t=\sigma(W_r(X)) \odot C_{t-1}$
   b. W_r: FCNN
   c. $C_{t-1}$: Cell state from previous time step
3. Update Rule:
   a. $C_t=u_t+r_t$ The final prediction can be made by taking the output from the multi-signal memory aggregator 1560 and passing this information through a decision making neural network 1570, 1670. Different decisions can be made simultaneously by feeding the multi-signal memory output in parallel through several different layers. The different kinds of decision making are described in conjunction with FIG. 17.

Model Training Flowchart

Figure 19:
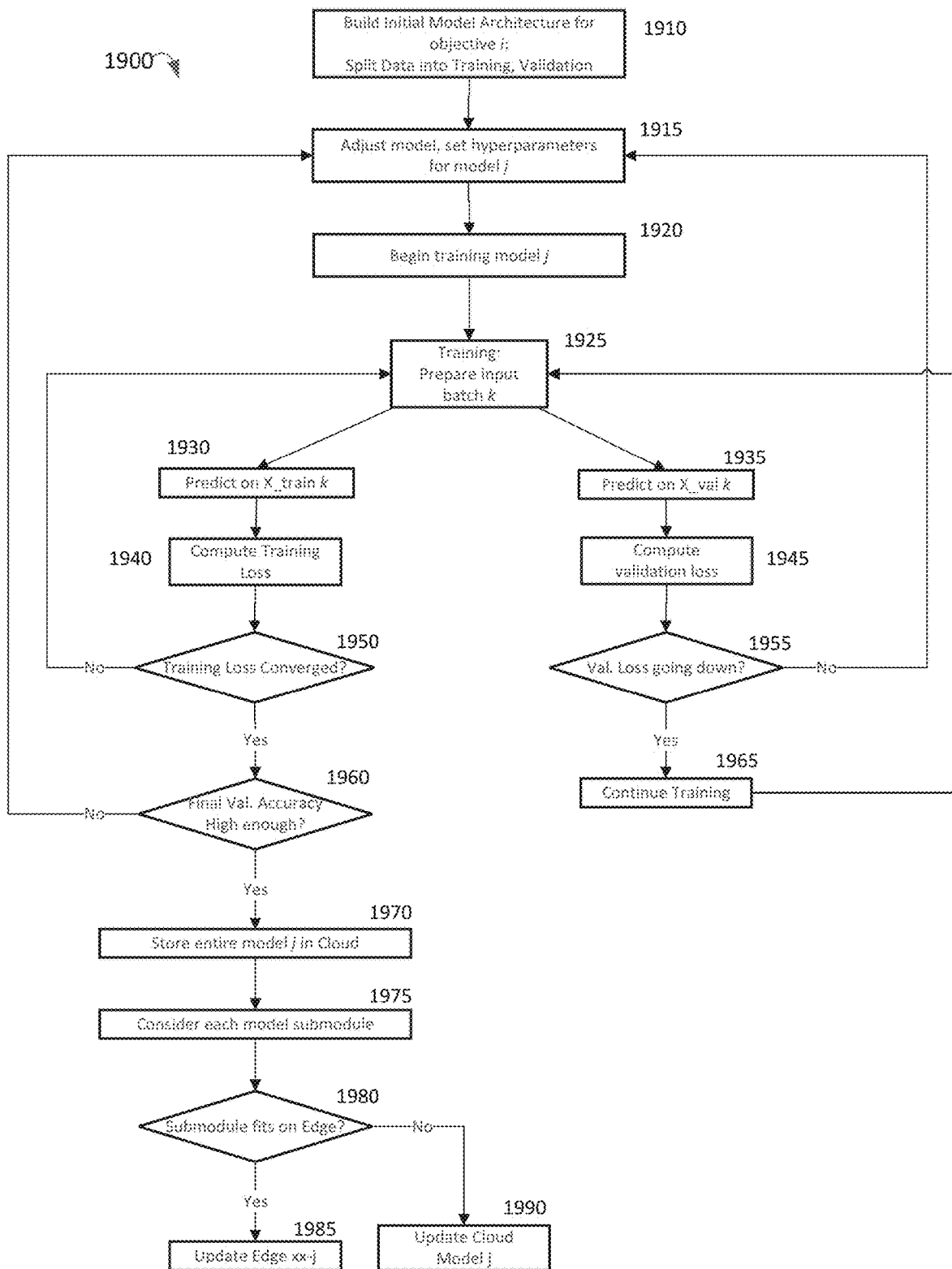
FIG. 19 is a flowchart of an embodiment of an example flow for building an initial model architecture for a particular objective.

The flowchart illustrated in FIG. 19 depicts a process 1900 of training, evaluating, and deploying the machine learning models for the system 100. First, an initial architecture is chosen for the particular model based on the desired objective, such as objective i. Then, an annotated offline dataset is randomly divided into separate training and validation subsets. These sub-steps are included at a step 1910. Before training, the model hyperparameters are chosen (for example, size of each training batch, learning rate, regularization penalties, etc.) at a step 1915 and the training of model j begins at a step 1920.

"Model J" refers to the model during a particular phase of architecture and hyperparameter optimization. At a training step 1925, the model makes a prediction on a training batch 1930 and a validation batch 1935. The output is compared with ground truth labels for that batch, and a loss is computed for that batch with respect to both the training 1940 and validation 1945 batches. The validation set is not used for updating model parameters, but only to monitor training progress to evaluate how well the model generalizes on unseen data. The training and validation losses are monitored together to evaluate model overfitting. For example, a high validation loss with a low training loss often signifies overfitting to the training set, meaning that the model will not generalize well to unseen data. Using a machine learning algorithm like gradient descent, the model parameters are updated as a function of training loss, with the goal of decreasing the loss for the next training iteration. This training cycle of predict-compare-update continues until either the training loss converges as determined at a decision step 1950, or the validation loss stops decreasing as determined at a decision step 1955. If the training loss converges, the final validation accuracy is compared at a decision step 1960 with a pre-determined threshold for the particular task. If the validation accuracy is too low, a new set of hyperparameters are chosen using a method such as Bayesian optimization. Hyperparameters are also reconfigured if the validation loss stops decreasing.

When the final validation accuracy is high enough, the entire model is stored in the cloud at a step 1970. Then at a step 1975, for each submodule (for example, FIG. 10 contains many LSTMs), a determination is made by a decision step 1980 as to whether the submodule will fit in memory on the edge device 1030, 1050. If the submodule requires too much memory or processing power or high computational time (inference time), it is designated for cloud computation at a step 1990. Otherwise, if it is suitable for deployment on the edge device, then that particular model is updated on the edge at a step 1985. In some embodiments, all edge system may communicate their available resources to the cloud.

Skilled technologists will understand that information and signals may be represented using any of a variety of different technologies and techniques. For example, data, instructions, commands, information, signals, bits, symbols, and chips that may be referenced throughout the above description may be represented by various types of data and/or signals.

Skilled technologists will further appreciate that the various illustrative logical blocks, modules, circuits, methods and algorithms described in connection with the examples disclosed herein may be implemented as electronic hardware, computer software, or combinations of both. To clearly illustrate this interchangeability of hardware and software, various illustrative components, blocks, modules, circuits, methods and algorithms have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the examples disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The methods or algorithms described in connection with the examples disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other suitable form of data storage medium now known or made available in the future. A storage medium may be connected to the processor such that the processor can read information from, and write information to, the storage medium. In the alternative, the storage medium may be integral to the processor. The processor and the storage medium may reside in an ASIC.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, rather than sequentially.

The previous description of the disclosed examples is provided to enable any person skilled in the art to make or use the present invention. Various modifications to these examples will be readily apparent to those skilled in the art, and the generic principles defined herein may be applied to other examples without departing from the spirit or scope of the invention. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope. Thus, the present invention is not intended to be limited to the examples shown herein but is to be accorded the widest scope consistent with the principles and novel features disclosed herein.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the detailed description of the preferred embodiments having reference to the attached figures, the invention not being limited to any particular preferred embodiment(s) disclosed.

What is claimed is:

1. A system for processing human related data to make personalized and context aware decisions with distributed machine learning at an edge and a cloud, the system comprising:
    a plurality of edge computing devices configured to communicate data with each other, the plurality of edge computing devices physically spaced apart from each other;
    at least three sensory devices comprising first, second and third sensory devices configured to sense a patient's physiological signal in real time to generate a first sensed signal, a second sensed signal and a third sensed signal and communicate the first, second and third sensed signals to an edge computing device nearest available to the first, second and third sensory devices among the plurality of edge computing devices; and
    a core cloud network configured to communicate with the edge computing devices or the at least three sensory devices,
    the nearest available edge computing device being in data communication with the core cloud network and configured to:
        receive the first, second and third sensed signals from the first, second and third sensory devices;
        determine when the first sensed signal exceeds a first threshold for a first predetermined time;
        determine when the second sensed signal exceeds a second threshold for a second predetermined time;
        determine when the third sensed signal exceeds a third threshold for a third predetermined time;
        correlate the first sensed signal and the second sensed signal to generate a first correlation pattern;
        determine a lag time between the first sensed signal exceeding the first threshold and the second sensed signal exceeding the second threshold;
        provide the first correlation pattern and the lag time as inputs to a first long short term memory (LSTM) neural network;
        correlate the second sensed signal and the third sensed signal to generate a second correlation pattern;
        provide the second correlation pattern to a second LSTM neural network as an input;
        control the first LSTM neural network and the second LSTM neural network to provide outputs; and
        map the patient to a stage of a medical condition based at least in part on the first correlation pattern, the lag time and the second correlation pattern.

2. The system of claim 1, wherein the nearest available edge computing device is further configured to:
    correlate the first sensed signal and the third sensed signal to generate a third correlation pattern;
    provide the third correlation pattern to a third LSTM neural network as an input;
    collect a history of states from each of the first, second and third LSTM neural networks;
    analyze the history of the states using an attention network such that an output of the attention network learns interactions across time and across signals; and
    summarize a history of the interactions using a multi-signal memory aggregator such that an output of the multi-signal memory aggregator is fed into a decision making module to map the patient to the stage of the medical condition based on the summarized history of the interactions.

3. The system of claim 2, wherein the nearest available edge computing device comprises:
    a first feature extractor configured to determine when the first sensed signal exceeds the first threshold for the first predetermined time;
    a second feature extractor configured to determine when the second sensed signal exceeds the second threshold for the second predetermined time;
    a third feature extractor configured to determine when the third sensed signal exceeds the third threshold for the third predetermined time; and
    a first correlator configured to correlate the first sensed signal and the second sensed signal to generate the first correlation pattern and determine the lag time between the first sensed signal exceeding the first threshold and the second sensed signal exceeding the second threshold as inputs to a first cell in the first LSTM neural network in an LSTM bank,
    wherein the third feature extractor is configured to directly feed the third sensed signal to a first cell in the second LSTM neural network in the LSTM bank,
    wherein the first correlator is further configured to generate additional first correlation patterns over time into additional different cells of the first LSTM neural network,
    wherein the third feature extractor is further configured to provide additional instances over time when the third sensed signal exceeds the third threshold as input signals into additional different cells of the second LSTM neural network,
    wherein the cells of each of the first LSTM neural network and the cells of the second LSTM neural network in the LSTM bank are configured to be fed into a fully connected neural network to generate attention map coefficients that are component-wise multiplied with the cells of the first LSTM neural network and the cells of the second LSTM neural network to generate an attention map,
    wherein the attention map is configured to be fed into the multi-signal memory aggregator to aggregate multiple signal memories over time to prepare an optimal input into the decision making module, and
    wherein the decision making module is configured to make a decision to map the patient to the stage of the medical condition based on the optimal input received from the multi-signal memory aggregator.

4. The system of claim 1, wherein the first sensed signal, the second sensed signal and the third sensed signal are of different modalities, wherein the first correlation pattern, the second correlation pattern, a state of the first LSTM neural network and a state of the second LSTM neural network are configured to be fed into a first multi-modal LSTM neural network, wherein the second correlation pattern, the third correlation pattern, the state of the second LSTM neural network and a state of the third LSTM neural network are configured to be fed into a second multi-modal LSTM neural network, and wherein the states of the first, second and third LSTM neural networks, and outputs of the first multi-modal LSTM neural network and the second multi-modal LSTM neural network are configured to be fed into a multi-signal memory aggregator.

5. The system of claim 4, further comprising an attention function processor configured to:
receive one of the first, second and third sensed signals as an input signal;
find one or more certain patterns of the input signal; and
categorize the input signal and generate the attention map corresponding to the certain patterns before being correlated.

6. The system of claim 4, further comprising an attention function processor configured to:
receive one of the first, second and third sensed signals as an input signal;
find one or more certain patterns of the input signal; and
categorize the input signal and generate the attention map corresponding to the certain patterns before being an input of one of the first or second multi-modal LSTM neural networks.

7. The system of claim 3, wherein the nearest available edge computing device is configured to present the attention map to a healthcare professional as documentation to support the determination of the stage of the patient's medical condition.

8. The system of claim 2, wherein the decision making module comprises at least one fully connected neural network.

9. The system of claim 8, wherein the decision making module is configured to generate a scalar quantified risk score.

10. The system of claim 8, wherein the fully connected neural network comprises a scaled sigmoid activation function.

11. The system of claim 8, wherein the decision making module comprises an argmax function configured to operate on an output of the fully connected neural network.

12. The system of claim 11, wherein the decision making module is configured to generate a binary format prediction.

13. The system of claim 11, wherein the fully connected neural network comprises a unit for each class of a multiple-class classification and wherein the output of the argmax function is a probability of the input data belonging to each class of the multiple-class classification.

14. The system of claim 2, wherein the nearest available edge computing device comprises at least one of the first to third LSTM neural networks and the decision making module.

15. The system of claim 1, wherein the nearest available edge computing device is configured to buffer and align at least one of the first, second and third sensed signals before being correlated.

16. An edge computing device for processing human related data to make personalized and context aware decisions with distributed machine learning at an edge and a cloud, the edge computing device comprising:
a memory storing computer executable instructions; and
a processor in data communication with the memory and, when executed by the executable instructions, configured to:
receive a first sensed signal, a second sensed signal and a third sensed signal obtained in real time from sensing a patient's physiological signal from first, second and third sensory devices,
determine when the first sensed signal exceeds a first threshold for a first predetermined time,
determine when the second sensed signal exceeds a second threshold for a second predetermined time,
determine when the third sensed signal exceeds a third threshold for a third predetermined time,
correlate the first sensed signal and the second sensed signal to generate a first correlation pattern,
determine a lag time between the first sensed signal exceeding the first threshold and the second sensed signal exceeding the second threshold, and
correlate the second sensed signal and the third sensed signal to generate a second correlation pattern;
a first long short term memory (LSTM) neural network configured to receive the first correlation pattern and the lag time from the processor; and
a second long short term memory (LSTM) neural network configured to receive the second correlation pattern from the processor,
wherein the processor is further configured to:
control the first LSTM neural network and the second LSTM neural network to provide outputs; and
map the patient to a stage of a medical condition based at least on the first correlation pattern, the lag time and the second correlation pattern.

17. The edge computing device of claim 16, wherein the processor is further configured to:
correlate the first sensed signal and the third sensed signal to generate a third correlation pattern; and
provide the third correlation pattern to a third LSTM neural network as an input,
wherein the processor is configured to make a decision on outputs of the first, second and third LSTM neural networks.

18. The edge computing device of claim 17, wherein the processor is further configured to make the decision by performing a scattering function on the outputs of the first, second and third LSTM neural networks.

19. The edge computing device of claim 16, wherein the processor is further configured to:
correlate the first sensed signal and the third sensed signal to generate a third correlation pattern;
provide the third correlation pattern to a third LSTM neural network as an input;
collect a history of states from each of the first, second and third LSTM neural networks;
analyze the history of the states using an attention network such that an output of the attention network learns interactions across time and across signals;
summarize a history of the interactions using a multi-signal memory aggregator; and
feed an output of the multi-signal memory aggregator into a decision making module to map the patient to the stage of the medical condition based on the summarized history of the interactions.

20. The edge computing device of claim 16, wherein the processor comprises:

a first feature extractor configured to determine when the first sensed signal exceeds the first threshold for the first predetermined time;

a second feature extractor configured to determine when the second sensed signal exceeds the second threshold for the second predetermined time;

a third feature extractor configured to determine when the third sensed signal exceeds a third threshold for a third predetermined time; and a first correlator configured to correlate the first sensed signal and the second sensed signal to generate the first correlation pattern and determine the lag time between the first sensed signal exceeding the first threshold and the second sensed signal exceeding the second threshold as inputs to a first cell in the first LSTM neural network in an LSTM bank, wherein the third feature extractor is configured to directly feed the third sensed signal to a first cell in the second LSTM neural network in the LSTM bank, wherein the first correlator is further configured to generate additional first correlation patterns over time into additional different cells of the first LSTM neural network, wherein the third feature extractor is further configured to provide additional instances over time when the third sensed signal exceeds the third threshold as input signals into additional different cells of the second LSTM neural network, wherein the cells of each of the first LSTM neural network and the cells of the second LSTM neural network in the LSTM bank are configured to be fed into a fully connected neural network to generate attention map coefficients that are component-wise multiplied with the cells of the first LSTM neural network and the cells of the second LSTM neural network to generate an attention map, wherein the attention map is configured to be fed into a multi-signal memory aggregator to aggregate multiple signal memories over time to prepare an optimal input into a decision making module, and wherein the decision making module is configured to make a decision to map the patient to the stage of the medical condition based on the optimal input received from the multi-signal memory aggregator.

21. A method of processing human related data to make personalized and context aware decisions with distributed machine learning at an edge computing device in communication with a cloud, the method comprising:

receiving, at a processor of the edge computing device, a first sensed signal, a second sensed signal and a third sensed signal obtained from sensing a patient's physiological signal from first, second and third sensory devices;

determining, at the processor, when the first sensed signal exceeds a first threshold for a first predetermined time;

determining, at the processor, when the second sensed signal exceeds a second threshold for a second predetermined time, determining, at the processor, when the third sensed signal exceeds a third threshold for a third predetermined time;

correlating, at the processor, the first sensed signal and the second sensed signal to generate a first correlation pattern, determining, at the processor, a lag time between the first sensed signal exceeding the first threshold and the second sensed signal exceeding the second threshold;

correlating, at the processor, the second sensed signal and the third sensed signal to generate a second correlation pattern;

receiving, at a first long short term memory (LSTM) neural network of the edge computing device, the first correlation pattern and the lag time;

receiving, at a second LSTM neural network of the edge computing device, the second correlation pattern;

controlling, at the processor, the first LSTM neural network and the second LSTM neural network to provide outputs; and mapping, at the processor, the patient to a stage of a medical condition based at least on the first correlation pattern, the lag time and the second correlation pattern.

22. The method of claim 21, further comprising:

correlating, at the processor, the first sensed signal and the third sensed signal to generate a third correlation pattern;

receiving, at a third LSTM neural network of the edge computing device, the third correlation pattern;

collecting, by the processor, a history of states from each of the first, second and third LSTM neural networks;

analyzing, at an attention network of the edge computing device, the history of the states to learn interactions across time and across signals;

summarizing, at a multi-signal memory aggregator of the edge computing device, a history of the interactions;

feeding, by the processor, an output of the multi-signal memory aggregator into a decision making module of the edge computing device; and mapping, at the decision making module, the patient to the stage of the medical condition based on the summarized history of the interactions.

23. The method of claim 21, further comprising:

receiving first correlation pattern inputs at a first cell of the first LSTM neural network in an LSTM bank;

directly receiving the third sensed signal when the third sensed signal exceeds the third threshold at a first cell in the second LSTM neural network in the LSTM bank;

receiving additional first correlation patterns over time into additional different cells of the first LSTM neural network;

receiving, by the processor, additional instances over time when the third sensed signal exceeds the third threshold as input signals into additional different cells of the second LSTM neural network;

generating, by an attention network of the edge computing device, attention map coefficients based on the cells of each of the first LSTM neural network and the cells of the second LSTM neural network in the LSTM bank to be fed into a fully connected neural network;

generating, by the attention network, an attention map based on the attention map coefficients that are component-wise multiplied with the cells of the first LSTM neural network and the cells of the second LSTM neural network;

feeding, by the processor, the attention map into a multi-signal memory aggregator that is configured to aggregate multiple signal memories over time; and mapping, at a decision making module, the patient to the stage of the medical condition based on the aggregated multiple signal memories received from the multi-signal memory aggregator.

24. The method of claim 21, wherein the edge computing device is a nearest available edge computing device to the patient among a plurality of edge computing devices comprising the first to third edge computing devices being in data communication with the cloud.

25. The method of claim 21, further comprising:
receiving a request for service from a sensory device of the patient;
locating the patient's sensory device;
determining that the edge computing device is a nearest available edge computing device to the patient sensory device of a plurality of edge computing devices comprising the first to third edge computing devices being in communication with the cloud; and
assigning a service slot to the patient's sensory device.

26. The method of claim 25, wherein determining the nearest available edge computing device comprises:
receiving, at the plurality of edge computing devices, a signal sent by the patient's sensory device;
measuring strengths of the signal received by the plurality of edge computing devices;
comparing the strengths of the received signal; and
determining an edge computing device to have a strongest signal strength as the nearest available edge computing device.

27. The method of claim 21, further comprising:
buffering and aligning one of the first sensed signal or the second sensed signal before the correlating.

28. The method of claim 21, further comprising:
finding one or more certain patterns of the first sensed signal or the second sensed signal; and
generating an attention map corresponding to the certain patterns before the correlating.

29. The method of claim 28, further comprising:
presenting the attention map to a healthcare professional as documentation to support the determination of the stage of the patient's medical condition.

30. A system for processing human related data to make personalized and context aware decisions with distributed machine learning at an edge and a cloud, the system comprising:

a plurality of edge computing devices configured to communicate data with each other, the plurality of edge computing devices physically spaced apart from each other;
at least two sensory devices comprising first and second sensory devices configured to sense a patient's physiological signal in real time to generate a first sensed signal and a second sensed signal and communicate the first and second sensed signals to a first edge computing device nearest available to the first and second sensory devices among the plurality of edge computing devices; and
a core cloud network configured to communicate with the edge computing devices or the at least two sensory devices,
the nearest edge computing device in data communication with the core cloud network and configured to:
receive the first and second sensed signals from the first and second sensory devices;
determine when the first signal exceeds a first threshold for a first predetermined time and subsequently determine when the second signal exceeds a second threshold for a second predetermined time;
correlate the first signal and the second signal to generate a first correlation pattern;
determine a lag time between the first signal exceeding the first threshold and the second signal exceeding the second threshold; and
provide the first correlation pattern and the lag time as inputs to at least two recurrent neural networks (RNNs) operatively connected to each other to provide an input to a decision making module to map the patient to a stage of a medical condition based at least on one or more of the first correlation patterns and the lag time.

* * * * *